US006402770B1

(12) United States Patent
Jessen

(10) Patent No.: US 6,402,770 B1
(45) Date of Patent: Jun. 11, 2002

(54) METHOD AND APPARATUS FOR PLACING AND MAINTAINING A PERCUTANEOUS TUBE INTO A BODY CAVITY

(75) Inventor: John W. Jessen, Seattle, WA (US)

(73) Assignee: Avatar Design & Development, Inc., Seattle, WA (US)

( * ) Notice: Subject to any disclaimer, the term of this patent is extended or adjusted under 35 U.S.C. 154(b) by 0 days.

(21) Appl. No.: 09/324,091

(22) Filed: Jun. 1, 1999

Related U.S. Application Data

(60) Provisional application No. 60/087,783, filed on Jun. 1, 1998.

(51) Int. Cl.$^7$ .................................................. A61B 17/34

(52) U.S. Cl. ....................................... 606/170; 606/185

(58) Field of Search ................................. 606/167, 170, 606/171, 174, 185, 108; 604/264, 96, 101, 103, 171, 280; 128/200.26, 207.29; 30/162

(56) References Cited

U.S. PATENT DOCUMENTS

| 4,291,690 | A | * | 9/1981 | Jessen | 128/207.29 |
| 4,438,768 | A | * | 3/1984 | Barrickman | 606/108 |
| 4,578,865 | A | * | 4/1986 | Keller | 30/304 |
| 4,617,929 | A | * | 10/1986 | Gill | 128/207.28 |
| 4,715,121 | A | * | 12/1987 | Sugiyama et al. | 30/253 |
| 4,791,725 | A | * | 12/1988 | Amagaya | 30/154 |
| 4,877,021 | A | * | 10/1989 | Higer et al. | 128/200.26 |
| 5,147,316 | A | * | 9/1992 | Castillenti | 604/164 |
| 5,337,481 | A | * | 8/1994 | Mears | 30/162 |
| 5,536,256 | A | * | 7/1996 | Yoon | 604/156 |
| 5,620,456 | A | * | 4/1997 | Sauer et al. | 606/185 |
| 6,086,606 | A | * | 7/2000 | Knodel et al. | 606/208 |

* cited by examiner

Primary Examiner—Jeffrey A. Smith
Assistant Examiner—Michael B. Priddy
(74) Attorney, Agent, or Firm—Patrick M. Dwyer

(57) ABSTRACT

Innovative disposable thoracostomy and cricothyrotomy trocar systems and new and improved methods for emergency management of upper airway obstructions and chest injuries are disclosed.

6 Claims, 19 Drawing Sheets

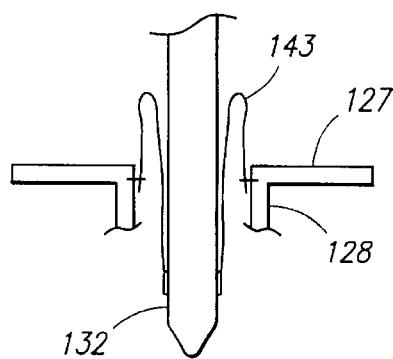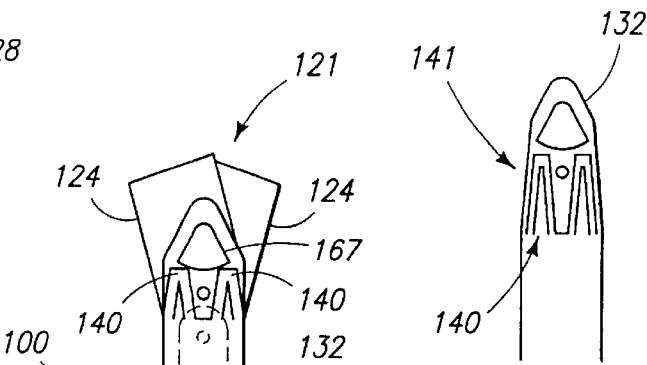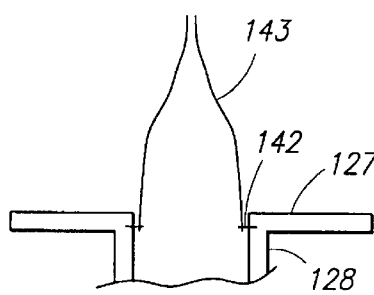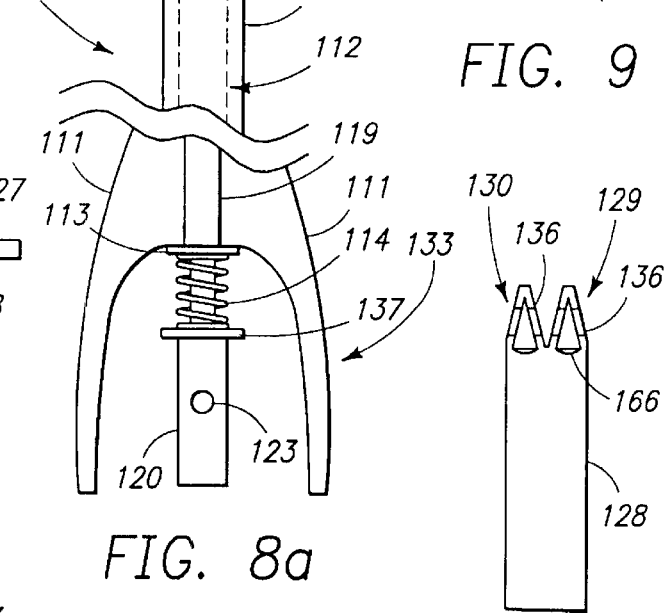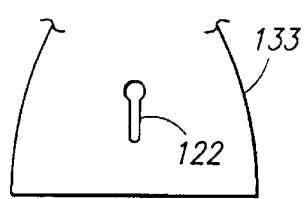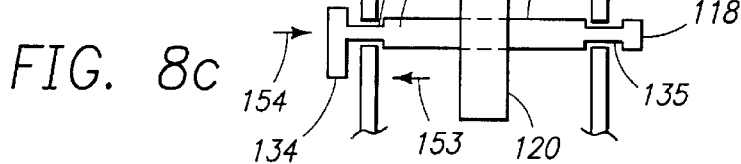

METHOD AND APPARATUS FOR PLACING AND MAINTAINING A PERCUTANEOUS TUBE INTO A BODY CAVITY

This application claims priority to provisional application No. 60/087,783 filed Jun. 1, 1998.

TECHNICAL FIELD

The invention relates to emergency airway devices and emergency thoracostomy devices; more particularly, it relates to trocar devices and method and apparatus for a establishing and maintaining an emergency opening to a body cavity.

BACKGROUND OF THE INVENTION

Cricothyrotomy

A cricothyrotomy is an emergency procedure performed on a choking person to admit air into the lungs via an opening made in the cricothyroid membrane. The cricothyroid membrane lies between the cricoid and thyroid cartilages of the voice box and is easily located by palpation of the larynx and trachea. Only the thin skin of the throat covers the membrane; no large blood vessels, glands, or other critical structures are normally encountered if this site is used. Though this area is not well-suited to long-term, auxiliary airway maintenance, it offers the safest and most direct access in times of emergency. Presently available devices and methods for performing an emergency cricothyrotomy, however, have serious drawbacks for inexperienced personnel and are of limited effectiveness.

A tracheotomy is a surgical procedure used to admit air into the lungs when the normal breathing passage is obstructed or otherwise ceases to function properly. Briefly stated, a tracheotomy usually involves an incision through the skin of the neck below the level of the voice box and careful manipulation of the thyroid gland and several large blood vessels to expose the trachea. A small circular opening is made in the trachea and an endotracheal tube is inserted to maintain the opening and provide an airway. A tracheotomy is the procedure of choice when an auxiliary airway is to be maintained for an extended period. It is a delicate operation requiring the skill and knowledge of a surgeon and the facilities of a hospital emergency room. Unfortunately, the services of a surgeon and hospital facilities are usually not immediately available to someone who is choking. Unless the patient is given means to breathe, he will die in approximately three minutes. There are well-established non-surgical techniques for removing a supralaryngeal airway obstruction which should be utilized, whenever possible, before any surgical technique is applied. However, these non-surgical methods have a limited range of applicability and are sometimes ineffective. Therefore, there is a need for a device which will enable a person with limited training to provide an emergency airway at any location where a choking emergency occurs.

The inventor earlier created a class of emergency retractable trocar devices to address some of the above concerns, and they are described in U.S. Pat. No. 4,291,690 issued Sep. 29, 1981. However, at the time of the earlier invention, some of the requirements for a practicable, minimally traumatic and fully controllable cricothyrotomy airway were not addressed or dealt with.

Firstly, it is now appreciated that placement of a large trocar (7–8 mm O.D.) through the skin into the trachea is extremely difficult if an adequate surgical incision and sharp dissection of the underlying tissue layers is not accomplished prior to insertion. Extensive testing of many cutting tip and blade designs demonstrates that any blade that is no wider than the inside diameter of the cannula mounted on the trocar shaft and that is merely pushed straight in without any substantial lateral motion will not make an incision that is wide enough to allow a short, straight cannula to be pushed into the upper tracheal airway without excessive force and without extreme danger of over penetration and subsequent crushing trauma to underlying tissues, no matter what the shape or length of the blade. Trauma to the larynx during cricothyrotomy is the primary cause of subglottic stenosis, the most common but preventable complication.

In addition, uncontrolled lateral motion of a blade during incision into the cricothyroid ligament space can cut the recurrent laryngeal nerve resulting in vocal cord paralysis, another major complication of poorly done cricothyrotomy. If a scalpel is used to make a stab incision into the airway, it must be subsequently removed and some type of retractor or tissue separator inserted to enable placement of an airway. When the blade is taken out, the various tissue layers are free to slip relative to one and the path of insertion into the airway can be lost. Re-establishment of the path of insertion can be traumatic and time consuming if not impossible without re-incision.

Secondly, a fixed blade on the end of a trocar can lacerate or penetrate the posterior tracheal wall and esophagus during insertion. This is a potentially fatal complication.

Thirdly, full control of the airway and the ability to forcefully ventilate the patient requires placement of an adequately sized cuffed tracheotomy tube.

What is needed is an improved trocar device to address these additional requirements and any other concerns that arise in such emergency situations.

Thoracostomy

Trauma is the third leading cause of death in the United States and the leading cause of death in young people. Blunt and penetrating chest injuries account for a large number of trauma related deaths. A tension pneumothorax is one of the leading causes of death from chest trauma. A tension pneumothorax occurs when a patient suffers chest injuries resulting in a tear of the lung. Air escapes and builds up under tension outside of the lung in the pleural space. The air under tension changes the dynamics of the circulatory system by impeding blood return to the heart, resulting in severe shock and death if not immediately corrected. This can occur during positive pressure ventilation, when diseased lungs rupture more frequently, following direct chest trauma secondary to fractured ribs. A tension pneumothorax often develops rapidly after the lung injury and therefore the treatment of the tension pneumothorax is an important part of most emergency training protocols.

When a patient develops a tension pneumothorax there is an emergent need to decompress the thorax. When a tension pneumothorax is suspected, a procedure known as needle thoracostomy is typically performed to release the tension. A needle thoracostomy utilizes a large needle or an IV catheter with a one-way flutter valve. The needle is thrust blindly through the anterior chest to decompress the pneumothorax emergently. This procedure, sometimes referred to as "placing a flutter valve", is routinely taught to physicians, nurses and paramedics during formal training, including the Advanced Trauma Life Support (ATLS) and Advanced Cardiac Life Support Courses (ACLS), courses given to most practitioners dealing with critically ill patients.

Although generally helpful, there are several drawbacks to the current needle thoracostomy procedure. The needle or IV catheter can easily lacerate the lung and produce further lung injury or hemothorax (bleeding into the chest). In fact, a chest tube must always be placed after a needle thoracostomy to treat the presumed needle injury from the procedure, even if the diagnosis of pneumothorax was incorrect! Most injuries to the lung produce some degree of hemothorax anyway, and that increases the chance that blood will clog the typically small caliber needle that is currently used. Today, most health care providers simply use an IV catheter or make-shift needles with balloons, finger cots, or slit finger tips of latex gloves on the end to decompress a tension pneumothorax.

In a typical scenario, a trauma patient with an injured lung develops profound shock after endotracheal intubation. This results because the air introduced under positive pressure escapes through the injured lung and a tension pneumothorax ensues. The paramedics would listen for decreased breath sounds, and if absent, would perform a needle thoracostomy by placing a needle or IV catheter through the side with the decreased breath sounds.

Another common scenario is the patient in extremis who fails to respond to resuscitation. As called for in the ATLS and ACLS protocols, needle thoracostomies are often performed to "rule out" a tension pneumothorax. While this can be successful when a tension pneumothorax is actually present, many patients are not completely decompressed because either the needle does not stay in position, the needle is too small in caliber to adequately decompress the thorax, or the needle has become clogged with blood and cannot continue to function.

In other situations, patients arrive at hospital with a clogged "flutter valve", or it has become ineffective because of the variable thickness of the chest wall, or it has fallen out or become displaced in transport. When this happens, a tension pneumothorax redevelops, suggesting at least that the current technology is inadequate.

A review of the medical literature reveals several reports of attempts to develop a device in the 1970's. The McSwain Dart is reported as a device that utilized a larger catheter and a tapered steel needle to decompress tension pneumothoracies. Despite an initial series of reports of the benefits by Dr. McSwain (see McSwain, JACEP 1977; 6(7):325–5; McSwain, Med. Instrum. 1982; 16(5);249–50; and Wayne, Ann. Surg., 1980; 191(6):760–2), the device does not appear to have caught on and does not appear to be currently in use. Independent critical review of the product criticized it as being dangerous because of the large steel needle's propensity to lacerate the lung.

The issue of the needles becoming dislodged deserves further discussion. Patients with tension pneumothoracies often have multiple injuries and are very ill. There is a lot going on in an attempt to resuscitate them, sometimes including cardiopulmonary resuscitation (CPR). An unsecured needle or IV catheter can easily fall out and be unnoticed in this situation. Furthermore, long transport times are common as patients are often transferred great distances to regional trauma centers for specialized care. If the needle is dislodged or becomes clogged with blood, air begins to build up in the chest under tension. Frequently, upon arrival at an emergency room and when a large bore chest tube is placed, a large gush of air is encountered, indicating that there was a large volume of air not released by the needle thoracostomy.

This background taken together suggests that, while needle thoracostomy may be immediately life saving, it often works only briefly and it involves multiple risks. The pathophysiology of a tension pneumothorax can reoccur and the patient can again deteriorate. While it is ideal to quickly place a large bore chest tube after a needle thoracostomy, this is not practical during long ambulance or airlift transports or when the patient is in the immediate care of health care providers who do not routinely place chest tubes.

In any event, the literature suggests that there are far more indications for chest tube insertion, such as in pneumothoracies, hemothoracies, pleural effusions and empyemas, than there are for emergent needle thoracostomy. As previously mentioned, placement of a chest tube is always recommended after a needle thoracostomy anyway because of potential hemothorax.

Non-retractable trocar chest tube insertion systems are also known. These are also generally considered dangerous and, although purchased by many hospitals, not often used by physicians. They involve the use of a hollow sharp metal trocar with a chest tube inside. After the skin is incised, the trocar is advanced through the lateral chest wall until the pleura is penetrated and the chest tube is advanced forward while the trocar is withdrawn. The danger lies in having a sharp pointed, non-retractable trocar in the chest where it can injure the lung or heart. Because this technique is considered dangerous, most surgeons employ the standard hemostat technique of chest tube insertion. This involves incising the lateral chest wall, dissecting a subcutaneous tunnel above the rib with the finger and instruments, and punching through into the pleural space. A tube is then grasped with a hemostat and inserted through this tunnel. Sutures are then used to close the large wound around the tube.

A novel retractable trocar thoracostomy system is needed to replace the current needle thoracostomy technique that is used in emergency situations for patients who have tension pneumothorax, and to replace current chest tube insertion devices and procedures, as described above. A retractable trocar should be quicker, easier and less traumatic than currently used techniques, provided, among other criteria, that the cutting mechanism used to enter the chest is designed not to injure deep structures.

DISCLOSURE OF THE INVENTION

Devices and methods disclosed herein solve both the cricothyrotomy and the thoracostomy problems discussed above by, among other things, incorporating a twin-bladed, retractable incision mechanism, mounted within the end of a trocar. That is, not only is the trocar retractable, but the two part blades themselves are retractable within each trocar. Such devices make a precise incision greater than the width of the included cannula that is delivered with the trocar, and preferably about twice as wide as the I.D. of the cannula.

A surgical cutting tool is disclosed. It has a "cam action" (the term defined further herein) retractable blade assembly with two blades, each with a blade edge and an angled blade point. Preferably, the blade assembly has two substantially identical blades each having an edge face with a single bevel cutting edge disposed at an angle to a longitudinal axis of the blade, each edge ending in a blade point at a distal end of the blade, each blade further having a pivot pin hole in a proximal region of the blade with a hole center lying on the blade axis. Also each blade has a cam slot distal to the pin hole with an distal cam slot center lying substantially on the blade axis and a proximal cam slot center lying substantially on a line between the pin hole center and the blade point. The two blades are pivotally mounted edge face to edge face upon the pivot pin engaged within both pin holes. The tool also has a cam pin, the cam pin relatively stationarily engaged (see below) within both cam slots, so that movement of the pivot pin in a distal direction urges the two blades to rotate their two blade points closer to each other in an extended configuration, and movement of the pivot pin in a proximal direction urges the two blades to rotate their two blade points further from each other in a closed or retracted configuration.

In the extended configuration, the two blades have overlapping blade points to form an extended blade profile, and the profile preferably has a relatively less sharp, "safe zone" (discussed further below) at its tip. The tool also has a spring and a pushrod engaging the blades to extend the blade assembly against spring resistance into a locked position when fully extended; the pushrod may advantageously be a wire, or other longitudinally flexible, but compression and stretch resistant, push-pull type linkage such as wire wound cable.

A improved cannula for surgical procedures is also provided. It is a self retaining cannula with a collapsible retention lattice at a distal end. In one aspect, the lattice is further comprised of struts, and the struts are formed in a partial frusto-conical (truncated cone shape) configuration at the distal end of the cannula. In another aspect, prior to assembly, the lattice structure is formed substantially flat, and the cannula is segmented, with cannula segments depending radially from the flat formed lattice. Alternatively, the cannula and lattice structure, after assembly, has four contiguous rectilinear zones defined by an intersecting pair of substantially perpendicular lines, a central portion of each of which is open or latticed.

A retractable trocar device is provided for placing and maintaining a percutaneous tube into a body cavity such as an airway or a chest cavity. The device has a cam action retractable blade assembly with two blades, each with its own blade edge and angled blade point. The blade assembly has two substantially identical blades each having an edge face with a single bevel cutting edge disposed at an angle to a longitudinal axis of the blade, each edge ending in a blade point at a distal end of the blade, the two blades pivotally mounted edge face to edge face upon a pivot pin, with the blade points overlapped in an extended configuration. The blade assembly of the trocar device desirably also has a "safe zone" at a tip of the extended configuration, as discussed above.

The trocar device has a handle enclosing at least a portion of a spring and a pushrod, with pushrod under spring tension or compression in an extended configuration, the pushrod engaging the blades to extend the blade assembly against spring resistance into a locked position when fully extended. There is also provided a releasable lock mechanism for the pushrod. Some embodiments of the trocar device have an additional tapered zone proximal to a distal end of a trocar shaft within which slides the pushrod. The trocar device has either a self retaining tubular cannula engaged for delivery upon a trocar shaft, or a self retaining expandable cannula folded and engaged upon a trocar shaft. There is also provided an optional self deploying, removable, one way exit valve foldably engaged upon a hub end of the cannula.

The cannula may alternatively be a multi-segmental flexible piece, the segments joined in the center by a geometrically regular network of filaments, the filaments shaped and conjoined in such a way as to enable the segments to be folded and interengaged into a substantially tubular shape with the filaments thereby forming an outwardly collapsible structure having at least two break lines. With this in mind, other geometrical arrangements will occur to those skilled in the art.

The inventor developed an earlier retractable trocar device that is described in U.S. Pat. No. 4,291,690 issued Sep. 29, 1981, and by this reference the text and drawings of this patent are herewith incorporated as if fully set forth herein.

The incision mechanism for an embodiment of the invention directed particularly toward cricothyrotomy has two identical single beveled blades that are pivotally mounted for cam action expansion with their cutting edge sides face to face and overlapped at their respective points when fully extended. They form a single pointed delta or "V" shaped edge when extended, with (looking edge on) one half beveled on the left and the other half beveled on the right, so that there is a double thickness, double beveled point in the center generally having a blade sharpness angle that is twice that of either single blade. The preferred profile of this delta cutting edge is about 100° because it is desirable to make as gentle a surgical incision and insertion as possible to avoid crushing trauma to the larynx, without using so sharp and long a point that there is any danger of penetration of the tracheal wall at full insertion. The size and generally cylindrical shape of the tracheal lumen also make it further desirable that the lateral-most points of such a cutting edge come to rest (at furthest insertion) at the widest point of the lumen, so to avoid lacerating the tracheal wall during incision. It has been found that a delta point of about 100° optimizes and addresses these concerns most favorably by presenting a relatively pointed and sharp edge for ease of incision, while maintaining a relatively short point length with lateral point spread no wider than a typical tracheal lumen.

In this embodiment, the trocar system or set is pushed straight into the cricothyroid ligament space at a right angle to the surface of the skin. Flutes extend through the length of the trocar and as soon as the airway is entered, a hissing sound can be heard indicating full penetration into the airway. At this point the index finger is moved to conveniently compress a trigger mechanism that releases a spring activated retractor which closes the blade mechanism and pulls it back into the trocar, thus producing a relatively blunt end. The tapered conical end of the trocar, upon which is preferably mounted a short 7.2 mm I.D. self-retaining, expandable airway cannula, centers the trocar within the cricothyroid ligament space and gently dilates the incision as the trocar is easily, controllably inserted.

In order to prevent over penetration during initial insertion if excessive force is used or the patient lurches suddenly, two penetration control bars extend down from the sides of the handle. The bars come to rest against the surface of the throat and effectively stop the advance of the blade. They are pulled back automatically into the handle as the spring-activated retractor pulls back the blades to allow complete insertion of the trocar.

It is desirable that the blade mechanism be closed prior to withdrawing the shaft from within the cannula. When this is not done, the outwardly extended blades can potentially jam and damage the cannula. In order to eliminate this possibility, a safety switch has been designed in that automatically sets off the spring-activated retractor if the operator tries to pull the shaft from the cannula but forgets to retract the blades first.

After the blades and penetration control bars have been retracted, the trocar is inserted fully, seating the hub of the airway cannula against the throat. At this point the trocar shaft is pulled out as tabs on the hub of the cannula are held against the throat. This action causes the end of the cannula, which is snapped into four retentive grooves on the end of the trocar shaft, to flare outwardly as the shaft is withdrawn, thus anchoring the preferably self retaining airway. The light finger spring action of the expanded plastic struts prevents expulsion of the tube as the patient forcefully exhales.

In order to fulfill the requirement that an adequately sized cuffed tracheotomy tube can be placed, the cannula is made so that its preferably thin walled quadrisegmental tube will dilate as the cuffed tube is pushed easily through it into the trachea.

The preferred tracheal cannula is preferably made of polypropylene. It is preferably molded in a relatively flat plane with the ends of the quadrisections joined in the center to a network of interconnecting struts or filaments that is stretched and folded up to form a basket weave-like pattern as the sections come together, overlapping like the petals of tulip, to form the percutaneous tube. The extracorporeal portion of the cannula comes together to form the manipulative tabs on the hub, leaving the cannula segments to form a long tapered, funnel-like throat whose inner surfaces wedge outwardly as the cuffed tube is pushed in. A short cylindrical "keeper", which fits over the assembled sections of the funnel to hold the cannula together, is preferably provided and shaped as a standard 15 mm resuscitator coupling. If placement of a cuffed tube is indicated, the keeper is removed to allow insertion and expansion of the cannula.

This device, described above for use in performing cricothyrotomy, may, with scale and relative dimensions modified, also be used for performing a thoracostomy.

A thoracostomy system is also disclosed that utilizes a large bore retractable trocar instead of a needle to decompress the thorax, with the trocar placed anteriorly, similar in location to current needle thoracostomies. This emergent decompressive thoracostomy trocar preferably includes a one-way valve so air could exit, but not enter the chest. In one embodiment there is provided a thin, flat elastic membranous sleeve preferably attached to the inside of the extracorporeal hub of the cannula, and which is inserted into the cannula during assembly of the device by insertion of the shaft into the cannula, thereafter to turn inside out with withdrawal of the shaft to make a one-way flutter valve. Where deemed medically appropriate, this system can also be attached to an air drainage system for definitive care of an isolated pneumothorax.

Preferably, a safe-ended incision mechanism is provided that is retracted upon entering the chest, thus avoiding the potential for internal injury during deployment. The incision mechanism for this embodiment of the invention directed particularly toward thoracostomy also has two identical single beveled blades that are pivotally mounted for cam action expansion with their cutting edge sides face to face and overlapped at their respective points when fully extended. They also form a delta or "V" shaped edge when extended, with (looking edge on) one halfbeveled on the left and the other half beveled on the right, so that there is a double thickness, double beveled point in the center generally having ablade sharpness angle that is twice that of either single blade.

The preferred profile of this alternate cutting edge is about a 135° delta shape with a small zone, preferably about 1 mm, at the double thickness, double beveled center of the delta edge. The edge of this small zone is preferably perpendicular to the long axis of the trocar shaft. This slower cutting, less pointed zone is generally the result of an additional grinding step on each blade point that takes off a tiny portion of each sharp blade tip, while leaving the newly ground tip at the same blade sharpness angle as the rest of the blade, but in a new plane slightly skewed with respect to the plane of the cutting edge, and are the preferred safe-ended mechanism referred to above. The shallower delta shape and this safe zone serve to limit the depth and danger of initial penetration, particularly with respect to the danger of damage to underlying internal organs. The rib cage is strong enough to sustain the forces necessary to incise the dense, relatively noncompliant intercostal tissues fixed between the ribs, and to dilate a chest tube channel with this relatively wider, less pointed, slower cutting edge. These intercostal tissues provide sufficient resistance to allow the necessary cleavage forces to be achieved and maintained during sharp dissection.

On the other hand, the highly compliant, soft, rubbery tissues of the underlying internal organs do not provide sufficient resistance (as does the rib cage) to the widely spread axial pressure of the plunging trocar to enable it to penetrate. Preferably, the thick tapered body of the trocar shaft starts only 5 mm behind the leading edge of the extended blade, further adding to the resistance to penetration of soft organs. In addition, this style point prevents accidental engagement and distortion of the blade tip by the superior border of the rib (in case it is bumped) during insertion.

Flattening the V shaped incising edge to about 135° spreads the force of insertion over a wider area and increases the amount of pressure that is needed to start penetration. Since the apex of the blade point is thus closer to the plane of the lateral blade ends, the blade point has to penetrate only about 5 mm to make a complete incision into the chest cavity. In this short distance, the soft underlying internal organs cannot produce enough resistance to the slower cutting delta edge to be punctured or cut. Significantly, the expanded or extended blade mechanism is closed and spring retracted into the trocar shaft at this point by the simple push of a button on the handle of the insertion tool and, as is also true of the cricothyrotomy device disclosed above, the trocar has a relatively blunt end throughout the rest of the insertion sequence.

The trocar is then fully inserted and then the trocar shaft is removed to leave in place an included 13 to 14 mm I.D. plastic delivery cannula. The cannula can then manually be directed to the portion of the chest where the chest tube needs to be inserted. The chest tube is then inserted through the cannula, and the cannula is removed (such as by the Seldinger Technique). The chest tube can then be hooked up to closed system drainage, if further deemed necessary. In situations when pleural adhesions are expected however, the hemostat technique can still be used if ultrasound equipment is not available to identify the exact location of the intrathoracic bolus of air or blood.

There are several advantages to the system presented herein. 1) Retractable trocars in general have shown themselves to be relatively safe in laparoscopic surgery and are therefore likely to be safer than the known system of plunging a large, nonretractable needle blindly into the chest. 2) There are no needles involved; this should appeal in emergency situations where high risk accidental skin-break exposures often occur. 3) The caliber of the related cannula is much larger than any needle, and therefore less prone to clogging with blood. 4) A novel self retaining cannula is preferably employed, successfully addressing the problem of needle displacement. 5) The one-way valve does not allow air to enter from outside the chest, which is advantageous in the non-intubated patient or when the diagnosis of a tension pneumothorax is after all incorrect.

In the disclosed system the smallest possible surgical lesion is produced in the process of applying any of the devices disclosed, resulting in less post-operative pain and faster healing; the chest tube can be placed with the fewest possible steps in the shortest possible time; and the incision produced will be just large enough to allow relatively easy placement through the incised tissue of a preferred 13–14 mm I.D. delivery cannula that is sized to facilitate installation of a 36 size French chest tube.

In addition, the relatively minimal size of the incision and the dilation of the incision channel by a preferably tapered trocar shaft retains natural tissue resiliency and causes the tissue to close tightly and directly appose the chest tube after the delivery cannula is withdrawn. This allows a negative intra-thoracic pressure to be reliably maintained without the need for sutures on either side of the chest tube to close gaps around it. An optional one way exit valve can be included as a removable attachment for the delivery cannula which makes it useful for reducing compression pneumothoracies and eliminates the need to perform a secondary thoracostomy after the standard needle puncture technique. If the location of the chest access needs to be changed, the trocar can be easily reassembled and reapplied.

Installation of the preferred self-retaining delivery cannula in a single stroke prevents the path of insertion into the chest cavity from being lost during the procedure. The end of the thin-walled cannula collapses and flares out as the blunted trocar shaft is pulled from within it. This anchors the cannula lightly within the chest cavity. A conventional chest tube can then be placed through it with no further manipulation of the tissues, whereas the conventional technique requires multiple penetrations and extensive tissue manipulation to insert the tube.

The differences between the very restrictive anatomy of the laryngeal hard structures and the vacuous depths of the chest cavity will allow a thoracostomy trocar to be inserted further during deployment, provided that the end can be made safe after initial penetration. Thus one alternate embodiment adds a tapered extension of the trocar shaft just behind a relatively smaller set of blades, the tapered extension progressively dilating the smaller resulting incision and thus causing the tissues to fit more tightly around the cannula and result in a smaller scar. This version has a preferred 13 mm shaft which tapers slowly down to 9 mm and has two 9 mm blades (rather than the preferred 13 mm blades of the other version). A self-retaining 13 mm I.D. delivery cannula is provided to fit it on either version, depending on how the collapsing struts on the end are unfolded after it is made.

There is a potentially large market for this system, as it could be used by paramedics, emergency physicians, trauma surgeons, ICU doctors and anesthesiologists, all of whom encounter patients with pneumothoracies. Furthermore, a device such as this would improve the comfort and safety of critically ill patients during air transport because the attendant changes in altitude are known to worsen the physiologic effects of pneumothoracies by changing the air pressure differential in the thorax. The product of the invention can even be stocked on the "code" carts or with other emergency equipment and therefore be immediately available. Code carts, used for emergency resuscitations in hospitals, are found in every patient care area, emergency room and operating rooms in every hospital as well as in many clinics. This product could easily be included with emergency equipment carried by paramedics and flight crews that care for injured patients prior to arrival to a hospital.

It will be appreciated that placement of a large (>10 mm O.D.) trocar through the skin into a body cavity (trachea, thorax, abdomen) is extremely difficult, if not impossible, if an adequate surgical incision and sharp dissection of the underlying tissue layers is not accomplished prior to insertion. Extensive testing of many cutting tip and blade designs demonstrates that any blade that is no wider than the inside diameter of the cannula mounted on the trocar shaft and that is merely pushed straight in without any substantial lateral motion will not make an incision that is wide enough to allow a short, straight cannula to be pushed through the body wall without excessive force and without extreme danger of over penetration and mutilation of underlying tissues, no matter what the shape or length of the blade. In addition, any uncontrolled lateral motion of a pointed blade during incision into the body cavity can lacerate organs which may be immediately underlying. The retractable cutting mechanism disclosed herein, that preferably makes an incision about twice as wide as the trocar shaft itself, enables easy and reliable insertion of the trocar.

As discussed above, the skin and body wall are well designed to resist puncture and penetration into body cavities. Only with adequate sharp surgical incision of the skin and underlying tissues can insertion of a large bore (10 mm+) percutaneous tube be easily, safely and reliably accomplished. Gentle, progressive dilation of the incision is desirable for installation of the tube. The disclosed design accomplishes incision, dilation and installation in one motion, one step, with one instrument, with anchoring and gentle retention of the preferred inserter sleeve/breathing tube/one-way valve combination accomplished as the shaft is withdrawn from within the cannula.

The tapered dilator segment of the trocar shaft is self-centering and insures axial force application during insertion, to prevent unwanted lateral motion and to prevent inadvertent deep organ penetration. A preferably built in tapered wound dilator, provided in varying sizes, transfers dilating forces from the tip of the trocar shaft to the sides of the cannula struts, due at least in part to preferred inletting of the collapsible cannula struts onto the trocar shaft. The resulting configuration locks the cannula onto the shaft and enables out folding of the self-retaining mechanism during withdrawal of the shaft.

For other applications, the retractable twin-bladed incision mechanism can be made in a large or miniature scale and can also be used to deliver tubes that are not expandable or are not self-retaining. The preferred spring loaded rod linkage which extends and retracts the blades can be made to any desired length and can be both flexible and activated remotely, as through a surgical endoscope or catheter. Therefore, without departing from the scope of the invention, the device could be modified by those skilled in the art for endoscopic microsurgical insertion of tubes or shunts which require a precise, controlled puncture into a body cavity.

BRIEF DESCRIPTION OF THE DRAWINGS

FIGS. 8a–c are a partial sectional schematic view of the device shown in FIG. 7.

FIG. 9 is a detail of an alternate embodiment of the device shown in FIG. 7.

FIG. 10 is an alternate embodiment of the cannula casting of the device shown in FIG. 7.

FIGS. 11a–b are schematic sectional views of the flutter valve aspect of the invention.

BEST MODE OF CARRYING OUT THE INVENTION

Figure 1:
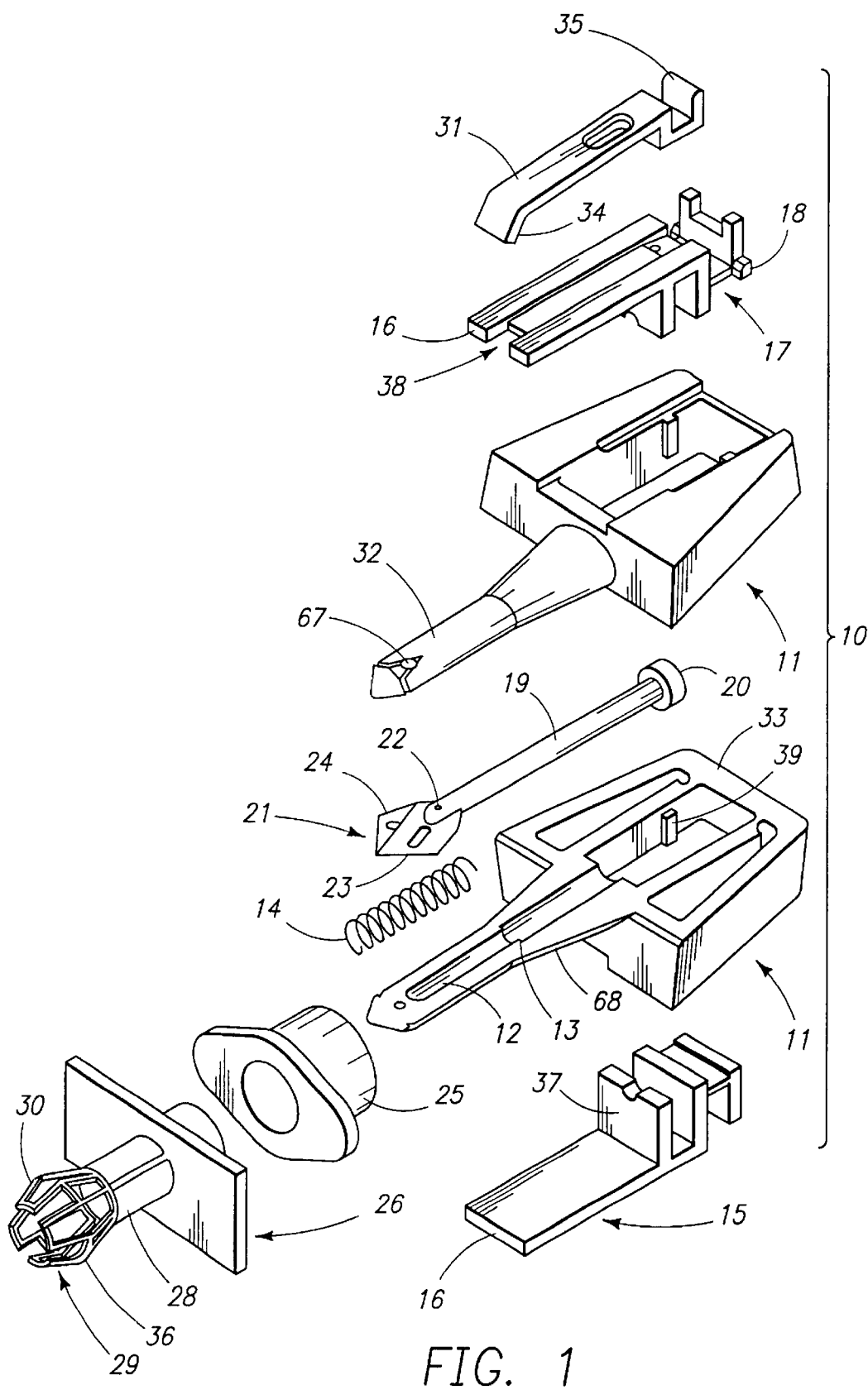
FIG. 1 is an exploded perspective view of a cricothyrotomy embodiment of the invention.

Turning now to the drawings, the invention will be described in a preferred embodiment by reference to the photographs and to the numerals of the drawing figures wherein like numbers indicate like parts. In this specification, the term proximal refers to a position relatively closer to the operator, and distal refers to a position relatively farther from the operator.

FIG. 1 is an exploded perspective view of a cricothyrotomy embodiment 10 of the invention. Blade assembly 21 preferably consists of two substantially identically formed stainless steel blades 24. One is flipped over with respect to the other and both are overlapped edge to edge, both pivotally mounted for co-rotation upon axis pin 22. Pin 22 is preferably a light press fit within an appropriate pin bore (not shown) in the distal end of rod 19. Each blade edge 43 (see also FIGS. 2,3,12 & 13) is precision ground in a single bevel to a preferred edge angle 62 of 17°. Each blade 24 for this embodiment is preferably 0.2 mm thick by 7.2 mm wide (and about twice that long), and made from chromium stainless steel, strip type 302, full hard, C-40/45. Those skilled in the art will appreciate that other blade thicknesses and widths and materials might be chosen for blades 24 without departing from the scope of the invention.

Figure 12A:
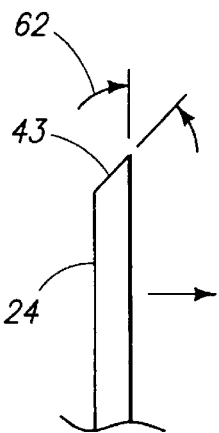
FIGS. 12a–c are partial side details of the blade edges of the blades shown in FIG. 2.
Figure 12C:
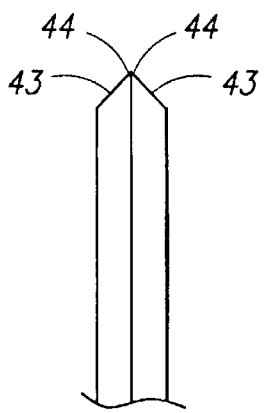
Figure 12B:
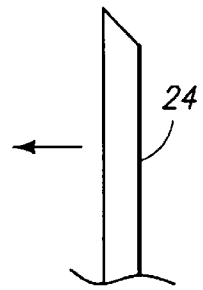
Figure 13B:
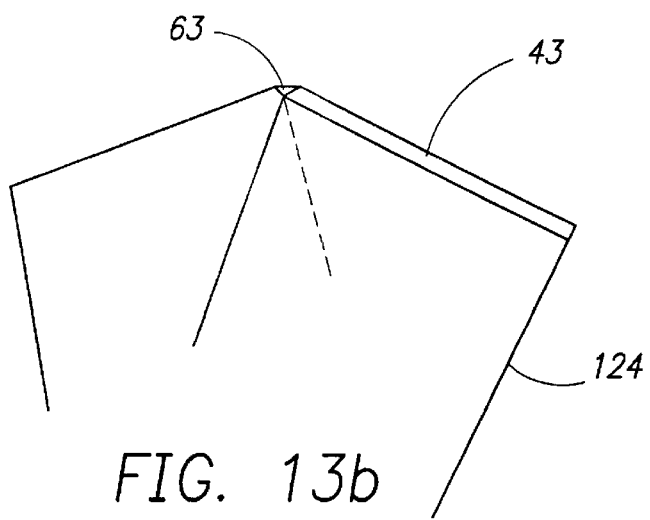

Each of the blades 24 has a blade angle 45 (FIG. 3b) at blade point 44 that is preferably about 65° in this embodiment at this point. At the apex of blade assembly 21 is delta point 46, where the overlapping blade points 44, upon full extension, preferably form for that region of blade assembly 21 a double blade thickness of 0.4 mm, with a preferred combined edge angle of 34°, roughly shaped like a chisel (FIG. 12c).

Rod head 20 rides engaged within the facing slots of mated rod retainer halves 15 and 17, so that in operation rod 19 and retainer halves 15 and 17 with their distal safety tabs 16 move as a unit, with rod 19 slidably engaged within rod channel 12 of mated body halves 11. Trocar 32 depends distally from handle 33, and channel 12 lies within trocar 32. Edges of trocar 32, and distal edges of handle 33 are preferably beveled at approximately 45 to form, when body halves 11 are mated, a flute 68 about 1 mm in depth all the way around the trocar and out the handle for release of air upon penetration into the body cavity. Trocar shaft 32 is desirably slightly radiused at its tip. Facet pair 67 near preferred conical tip of trocar 32 are formed by removing some of the conical shoulder to form two planar zones of somewhat slower wedging action than the wedging action of the rest of the conical angle. These facets 67 thus result in somewhat easier insertion start of trocar 32 through a body wall.

Figure 4C:
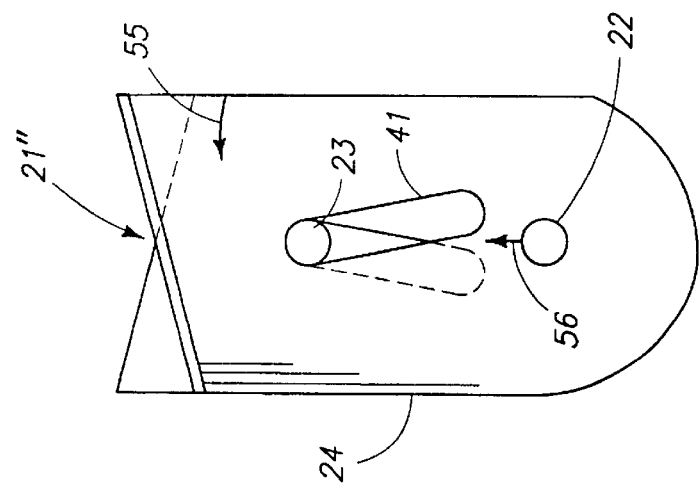
FIGS. 4a–c are plan view schematic sequences of the blades shown in FIG. 2.
Figure 4B:
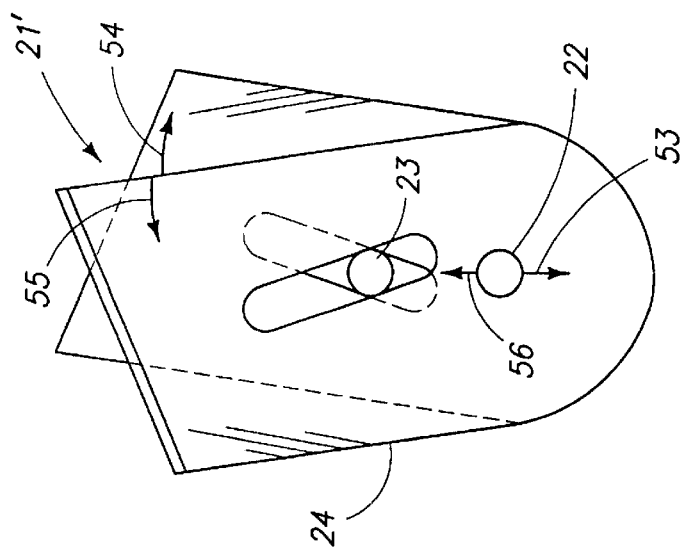
Figure 4A:
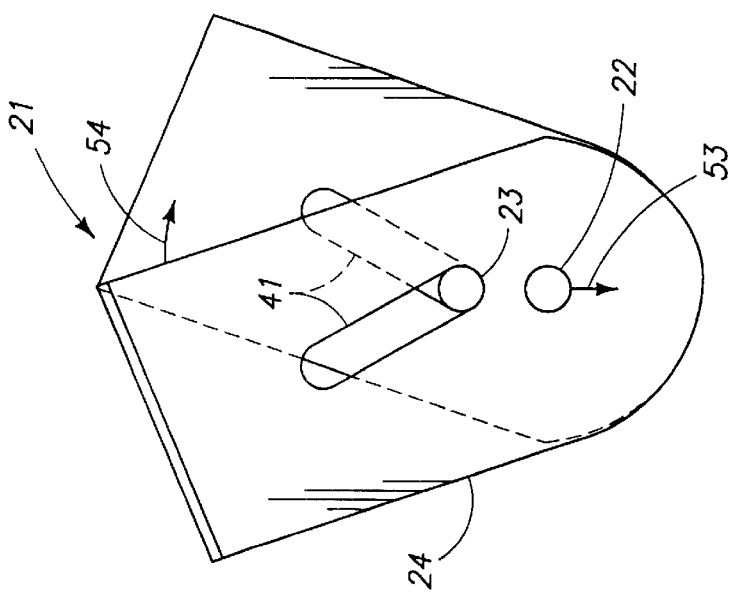

Cam pin 23 is engaged within both cam slots 41 of blades 24, and is also preferably a light press fit in an appropriate pin bore (not shown) in trocar halves 32, about one trocar's width back from the tip of trocar 32, such that, as rod 19 moves forward and back with its mounted blade assembly 21, cam pin 23 remains stationary relative to trocar 32, but can be seen as relatively slideable with respect to cam slots 41 (see FIGS. 4a–c). Cam pin 23 is preferably a rolled steel type of pin, and is positioned as close as possible to tip of trocar 32 without lying in any of the conical or faceted portion of the tip. Positioning further back will not disable the functioning of the device, but will make for a more aggressive (less leveraged) blade opening, and will generally require a proportionately longer blade length, together with a roughly proportionately heavier spring. It is of course the cam slots that move with the blade assembly, and not the cam pin, but some discussion and illustration may make more ready sense if the cam pin is viewed as relatively movable with respect to the cam slots.

Spring 14 is coiled around rod 19 and is seated in spring seat 13 at a point within channel 12. The other end of spring 14 is engaged by spring thrust face 37 of retainer halves 15&17, such that as rod 19 (with its retainer halves) is moved forward distally through channel 12, it does so against the urging of spring 14, compressing the spring and loading retainer lock tab 18 on retainer half 17 against retainer lock bar 39 (see FIGS. 5a–b) in handle 33. Desired spring force from spring 14 has not been quantified but selection of a stock spring of sufficient force to effectively retract blade assembly 21 should present no difficulty to the person skilled in the art.

Auto release bar 31 is mounted upon retainer half 17 so that release tab 34 slidably fits within tab slot 38 in safety tab 16, and blade lock release 35 fits within a corresponding slot at the proximal end of retainer 17. Retainer halves 15&17 are mated and slidably engaged within handle 33 in such a way that their fit within handle 33 is somewhat loose, allowing retainer 17,15 and release bar 31 to pivot with a slight rocking motion about a distal portion of the body material 11 of handle 33 (see pivot point reference 58 and body material 11 in FIG. 5b).

During assembly of device 10, and after the mating referred to above, and with rod 19 fully back (so blades are not extended), coupling 25 is assembled onto the proximal end of cannula assembly 26, which is then slid onto a proximal portion of trocar 32. Cannula assembly includes tabs 27, cannula 28 and collapsible strut network 29. Network 29 includes a number of struts 30 and living hinges 36 (see FIGS. 6a–e). It should be noted that in FIG. 1, strut network 29 is shown as partly collapsed, though that is not its typical state at assembly stage. When assembled, much of network 29 is enmeshed within the preferably molded in progressive inletting 40 (FIG. 6e) of the distal end of trocar 32 so that network struts 30 present little if any added resistance to body insertion of trocar 32, and are thus not prematurely collapsed upon insertion. Inletting 40 is progressive in that it is fully as deep at its distal-most portion as the network struts 30 are thick (same thickness as cannula, approximately 1 mm), but tapers to ever shallower inletting until at the proximal-most end of the inletting zone there is no inletting depth at all.

Figures 2, 3A, 3B:
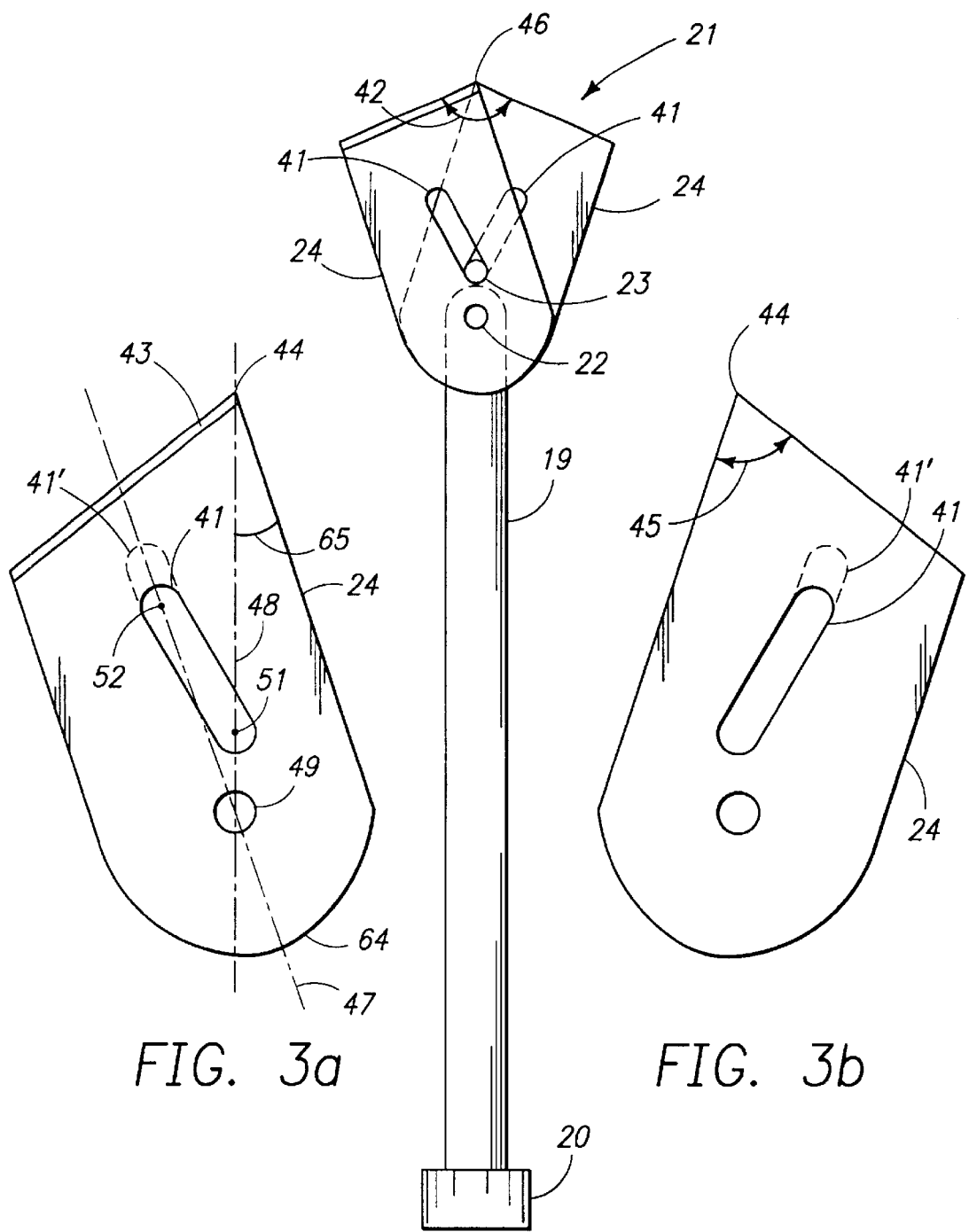
FIG. 2 is a detail partial plan view of a preferred blade mechanism of the invention.
FIGS. 3a–b are further plan view details of the blades shown in FIG. 2.

FIG. 2 is a detail partial plan view of the novel blade mechanism of the invention. This is a preferred mechanism, regardless of trocar embodiment; this discussion will apply for the most part to both classes of trocar disclosed herein, though reference numerals refer generally to the embodiment of FIG. 1; like parts for the embodiment of FIGS. 7&8 have like part numbers, with FIG. 7 having a 100 series numbers. Blades 24 are pivotally mounted on pivot pin 22 pressed into rod 19; blades 24 may generally pivot anywhere from a fully closed (retracted) engagement with each other, where the entire blades 24 are substantially overlapped (FIG. 4*a*) to a fully open (extended) engagement with each other, where along blade edges 43 only blade points 44 are overlapped (FIG. 2 and FIG. 4*c*), to anywhere in between (FIG. 4*b*). Fully open blades form a combined leading blade edge having a delta point 46, and a delta angle 42. When fully extended, blade assembly 21 has a blade delta angle 42 of about 95° to 100°.

As mentioned above, each blade 24 in blade assembly 21 is substantially identical to the other; they are preferably cut or stamped from the same specifications and are sharpened in the same manner, and on the same side. Only during assembly one is reversed with respect to the other and placed face to face as it where, or edge to edge, so that their respective blade edges 43 are touching at least at one or more points. Thus cam slots 41 that were identical at manufacture are now aligned in different directions (FIGS. 3*a–b*). Thus, with cam pin 23 fixed in the end of trocar 32 (not shown), it can be visualized that as rod 19 moves forward or back within trocar 32 blades 24 will be cammed open or closed with respect to each other (see FIGS. 4*a–c*) by the action of reciprocal cam slots 41 against relatively stationary cam pin 23.

As illustrated in FIGS. 3*a–b*, a number of variables combine to determine delta angle 42, including blade 24 width and length, relative positioning of blade axis pin bore 49 in heel 64 of blade 24, and blade angle 45. Heel 64 is preferably radiuses so that all points on the circumference of heel 64 are equidistant from the center of pin bore 49 (though other heel radius/pin center relationships may be made to serve as well). Top center 52 of cam slot 41 and the center of pin bore 49 are preferably aligned along a line 47 marking the longitudinal center of blade 24. Bottom center 51 of cam slot 41 and the center of pin bore 49 are preferably aligned along a line 48 between blade point 44 and pin bore 49 center. For purposes of estimation of delta angle 42, twice an angle 65 formed by blade side and line 48 may be deducted from twice blade angle 45. Optional cam slot extensions 41' (dotted lines) are doglegged back along line 47, and provide the optional capacity to fully withdraw blade assembly 21 into trocar 32. To best accommodate this optional feature, an extension of blade length of about the same length as the slot extension is desirable.

In this embodiment, cam slots 41 are preferably 0.468 inches in width (approximately the same as the diameter of cam pin 23), and 0.165 inches in length from top center 52 to bottom center 51. Cam slot 41 is preferably offset from line 47 by an angle of 10°, with top center 52 positioned 0.250 inches distal to center of pin bore 49. In other embodiments, whether larger blades and blade assemblies or smaller, dimensions are generally proportional to those described above, except notably for blade angle which may vary as disclosed herein and edge angle which generally does not change with blade size. Thus for example a blade twice as wide will generally be about twice as long, and other dimensions disclosed above also about twice as long.

With that in mind, and with the above instructive disclosure, those skilled in the art will be able to devise variations in blade delta angle 42, bearing in mind that, for any given set of blade width and height and relative pin bore positioning, angle 65 will not vary, and delta angle changes will depend on blade angle changes.

FIGS. 4*a–c* are plan view schematic sequences of the blades shown in FIG. 2. In 4*a*, blade assembly 21 has blades 24 are fully open, cam pin 23 is relatively stationary in bottom center of both cam slots 41, and pivot pin 22 in rod 19 (not shown) engaging both blades is withdrawn proximally in the direction indicated by arrow 53, causing blade 24 to move in the direction indicated by arrow 54 to begin greater overlap of the other blade. In 4*b*, blade assembly 21', pin 22 can move further in direction 53 to further move blade 24 in direction 54, or it can move back along arrow 56 to move blade 24 along arrow 55. In 4*c*, blade assembly 21", blade 24 having moved along arrow 54 to nearly fully overlap the other blade, pin 22 can now only move back along arrow 56 to move blade 24 back along arrow 55. Note that as pin 22 is withdrawn proximally (toward bottom of FIG. 4), cam pin 23 remains relatively stationary, but the entire blade assembly move further back (lower) progressing from 21 to 21' to 21". It is this action that withdraws or retracts the blade assembly, while at the same time closing it.

Figure 5A:
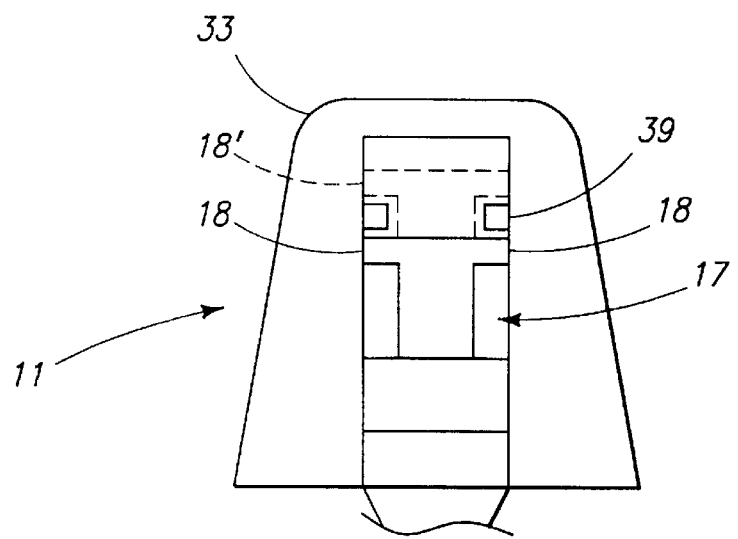
FIGS. 5a–b are detail partial sectional views of the blade lock and spring retraction mechanism of the device shown in FIG. 1.
Figure 5B:
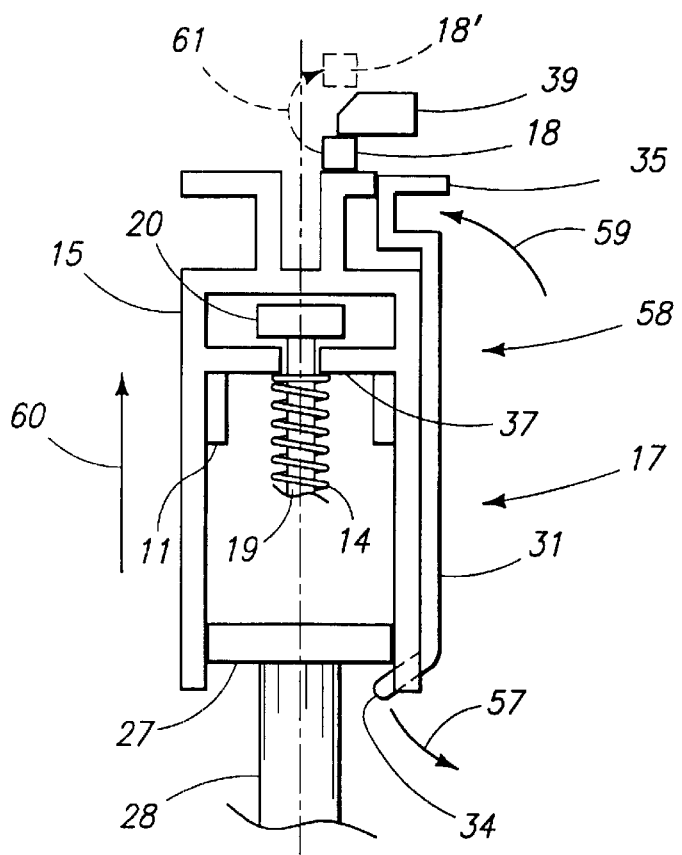

FIGS. 5*a–b* are detail partial sectional views of the blade lock and spring retraction mechanism of the device shown in FIG. 1. To extend and lock blade assembly 21 in its extended or open position, retainer assembly 15,17 is grasped and moved distally until lock tab 18 is caught and held in the position illustrated, just distal of lock bar 39. This can be seen from two views in both 5*a* and 5*b*. Lock tabs 18 are preferably paired and symmetrical, as are lock bars 39. Lock bar 39 is desirably radiuses approximately as shown to facilitate tab 18 sliding around bar 39 as rod 19 is extended distally. Tabs 18 are required to move slightly around bar 39 to achieve a locked and extended position, and this is facilitated by the previously mentioned loose fit of retainer 15,17 within body 11.

In the process of advancing retainer 15,17 distally, spring 14 is compressed and exerts a load tending to restore rod 19 to its unloaded proximal position in the direction of arrow 60. This may be released in one of two ways. Lock release 35 may be pressed, causing the retainer assembly to rock slightly in the direction of arrow 59 around a pivot point indicated approximately by reference mark 58 at the distal edge of body portion 11, so that tab 18 is impelled by spring 14 to travel roughly in the path indicated by dotted arrow 61 in 5*b* to end up at 18', thus releasing the lock and allowing spring 14 to withdraw retainer 15,17 and rod 19, and with them the blade assembly to retract and close the blades. Or, if the blades have not been earlier withdrawn prior to an attempt to withdraw trocar shaft 32 from cannula 28, tab 34 will encounter cannula tab 27 and be influenced in the direction of arrow 57, as the trocar shaft is withdrawn. Since release bar 31 is mounted on retainer half 17, rocking movement of tab 34 imparts the same rocking movement to the retainer as pressing release 35, and the unlock and retraction occurs as described above, thus automatically retracting the blades to prevent damage to the cannula from having inadvertently left them open.

Figure 6A:
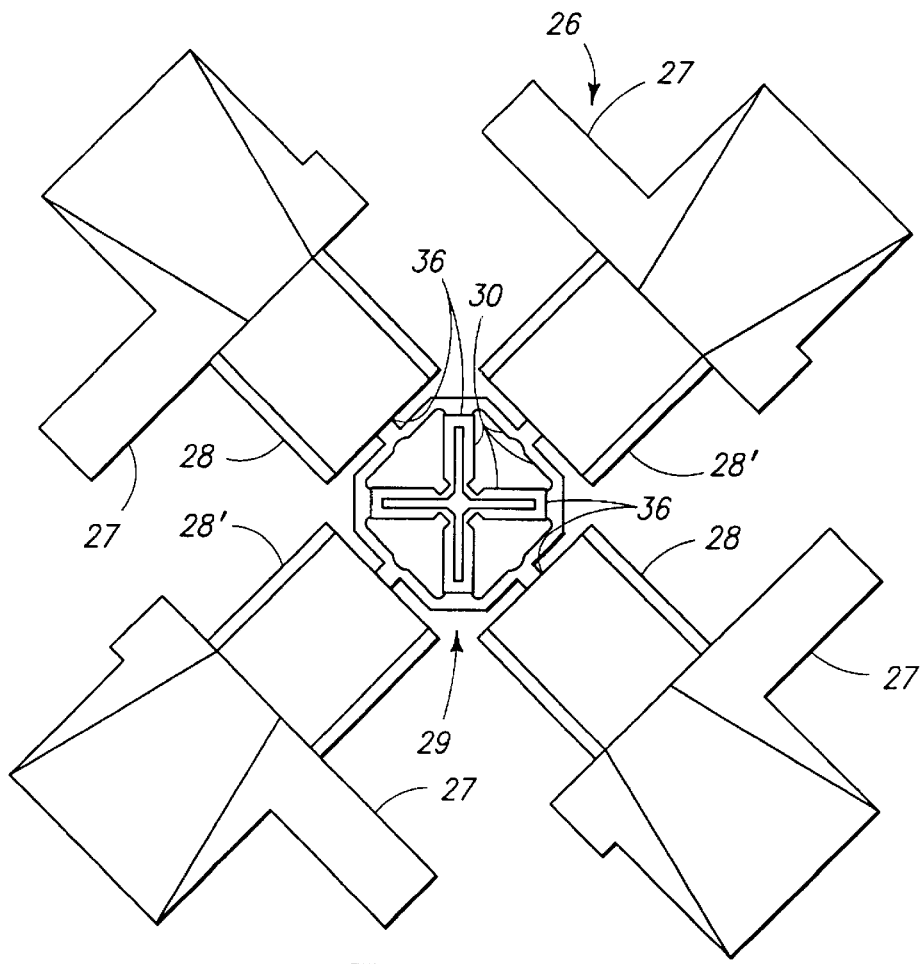
FIGS. 6a–e are plan, side and sectional views of an preferred quadrisegmental cannula shown in FIG. 1, shown first as molded and then as assembled.
Figure 6E:
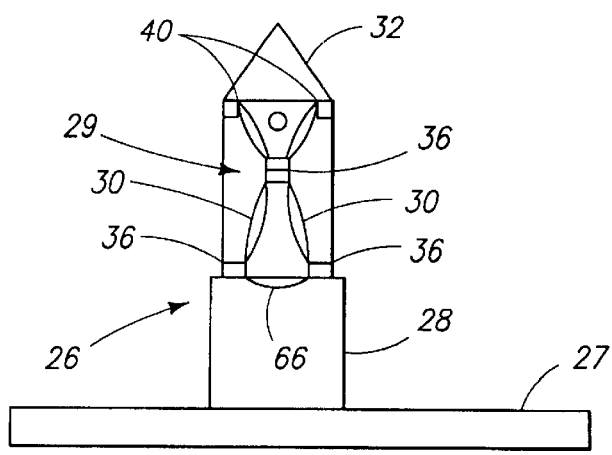
Figure 6B:
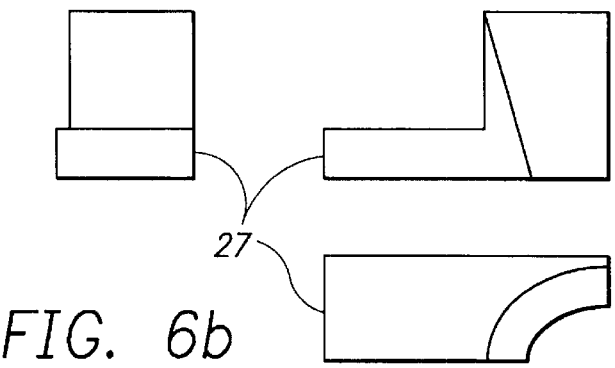
Figure 6C:
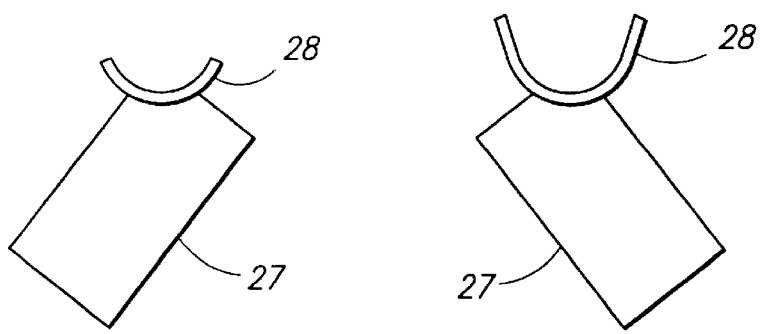

FIGS. 6*a–e* are views of an preferred quadrisegmental cannula 26 shown in FIG. 1, shown first in plan view as molded in 6a and then in side view as assembled and mounted on trocar in 6e. Cannula assembly 26 is actually preferably a single plastic injection molded piece, shown in plan view in FIG. 6a. Assembly 26 has four segments 27 that, when appropriately folded and assembled, form cannula 28 and cannula tabs 27. Each segment 27 is substantially identical, while portions 28 and 28' differ in that cannula segments 28 are greater in diameter than segments 28', so that when they are folded and assembled, with two segments 28' inside segments 28, the cannula 28 is double walled, but expandable. Tab segments 27 also preferably form a funnel shaped opening, with ¼ of the funnel in each segment. FIG. 6b illustrates, clockwise from upper left, a narrow end view, a broad end view, and a down-the-funnel view of each segment in the molded piece. FIG. 6c shows cannula segment end views of the smaller cannula segment (left) and the larger cannula segment (right).

The central portion of the molded piece in 6a is what will become, with folding and some stretching into the plane of the page of the figure, strut network 29 of cannula assembly 26. Note the presence of struts 30 and living hinges 36 in network 29. Living hinges are formed by generally stenotic regions along a network of struts, with one side of each such stenotic having a scribed or molded in line (not shown) along which the material may be more readily folded. In FIG. 6a these hinge lines are on the back of the part (back side of drawing) along the lines generally indicated by the numerals 36. Note that each strut 30 is also desirably separated from each other and from the living hinges 36 by intervening regions where the material is either also stenotic or angled substantially away from an adjoining strut structure. These stenoses and angles all facilitate the folding of the network necessary to change its shape from flat (6a) to generally conform to the shape of the trocar (6e). As the shape is changed, the stenoses and angles generally experience plastic deformation, while the struts 30 generally do not.

Figure 6D:
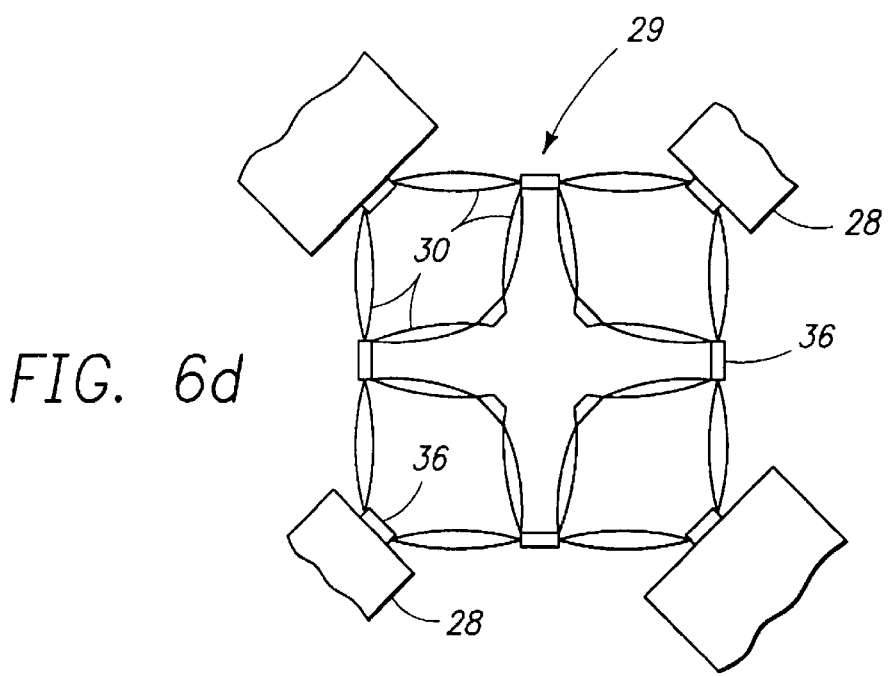

During the assembly folding, part 26 generally passes through apartially folded stage shown in FIG. 6d in which the generally octagonal shape of part 26 in 6a becomes (in plan view) the roughly square shape in 6d. In this view, what are intended eventually as the distal-most struts in the center of network 29 are already pulled out of the plane of the figure, and all of the stenoses and angles have experienced some deformation. The final cannula assembly 26 shape is shown in 6e (with cannula segments 28 and 28' conjoined to the double wall structure referred to above, and the tab and funnel segments 27 fully abutted) with struts 30 and hinges 36 progressively set into inletting 40 in trocar shaft 32. As an additional preferred aid to insertion without hanging up any of the cannula struts, bevel 66 is relieved in the cannula shoulder just proximal of strut network 29. It will be appreciated that, while this structure is shown with what will be seen as two sets of break lines (for eventual collapse), generally along two trocar circumferences determined by two hinge sets, additional break lines formed from hinges as disclosed, or the like, may also be provided without departing from the scope of the invention.

FIGS. 7a–d and 8a–c are photos and partial sectional drawings of the thoracostomy device 100 disclosed. Blade assembly 121, except for certain dimensions and features, is nearly identical to blade assembly 21 for the cricothyrotomy embodiment. Thus blade assembly 121 preferably also consists of two substantially identical overlapped edge to edge stainless steel blades 124, both pivotally mounted for co-rotation upon axis pin 22, pin 22 preferably a light press fit within an appropriate pin bore (not shown) in the distal end of rod 119. Likewise, each blade edge 43 (see also FIGS. 2,3,12&13) is precision ground in a single bevel to a preferred edge angle 62 of 17°. Each blade 124 for this embodiment is preferably 0.225 mm thick by 9 mm (in one embodiment, and 13 mm in another) wide, and approximately twice that long. Those skilled in the art will appreciate that other blade thicknesses, lengths and widths and materials might be chosen for blades 124 without departing from the scope of the invention.

Each of the blades 124 has a blade angle 45 (FIG. 3b) at blade point 44 that is preferably about 85° in this embodiment at this point. At the apex of blade assembly 21 is delta point 46, where the overlapping blade points 44, upon full extension, preferably form for that region of blade assembly 121 a double blade thickness of 0.450 mm, with a preferred combined edge angle of 34°, roughly shaped like a chisel (FIG. 12c). When fully extended, blade assembly 121 preferably has a blade delta angle 42 of about 130° to 135°.

Trocar 132 has its own progressive inletting 140 (like inletting 40 described above) to accommodate and receive cannula 128, with its own style of struts 130 and hinges 136 and bevel 166 (FIG. 10—shown as preferred variant 13 mm I.D. 'tapered' version of cannula, molded with network 129 already partially tapered—straight cylindrical cannula and network version shown in FIGS. 7a–d). Note presence of two lines of hinges (see especially in FIGS. 7b,c,d); as above, there may be more than two lines ('break lines') of hinges without departing from the scope of the invention. Trocar 132 also has tip facets 167 to make an easier insertion start, as discussed for device 10 under FIG. 1. Inside trocar 132 is channel 112, within which rod 119 is slidably engaged. Rod 119 extends back into handle 133, preferably comprised of body halves 111. Rod head 120, with thrust washer 137 receives the spring load of spring 114 seated upon washer 113. Rod head 120 has a channel 123 to slidably receive lock bar 139.

Rotating the view in 8a ninety degrees and again looking in section, the operation of lock bar 139 with rod head 120 and key holes 122 may be seen. Narrow portions of lock bar 139 provide relief 135, so that in the position illustrated, reliefs 135 are free to slide in through out and along the length of keyway 122 let into both sides of handle 133. When rod 119 is urged forward by thumb and finger pressure on button 134 and nub 118, spring pressure is increased and the blades extend and open. At the point of maximum extension, nub 118 is positioned over the wide portion of keyway 122 and, with some balance on button 134 so wide part of lock bar 139 just inside the button side relief 135 can be urged simultaneously into its wide part of the other keyway 122, nub 118 may be lightly pressed in the direction of arrow 153 into keyway 122, where it serves as a lock to hold the blades extended. To release the blades for spring loaded retraction, only button 134 need be pressed in the direction of arrow 154, thus presenting again the relief portions of lock bar 139 to keyway 122 so that rod head and rod may freely slide backward under the urging of spring 114.

Figure 7A:
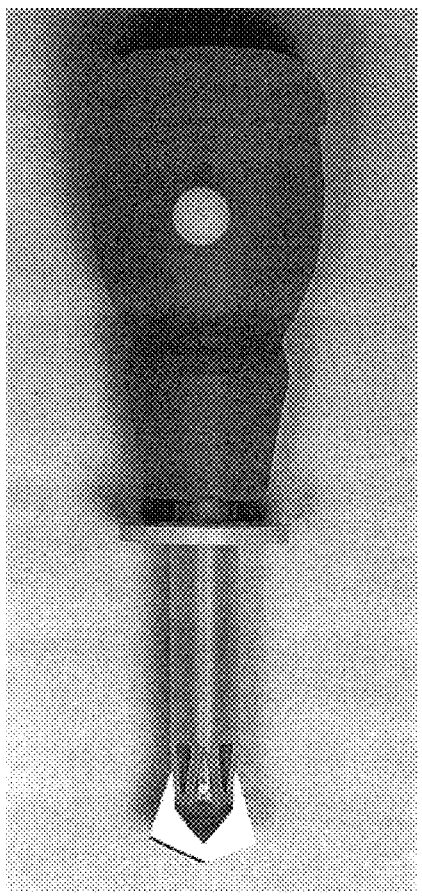
FIGS. 7a–d are photographs of an alternate thoracostomy embodiment of the invention, in sequence of operation.
Figure 7B:
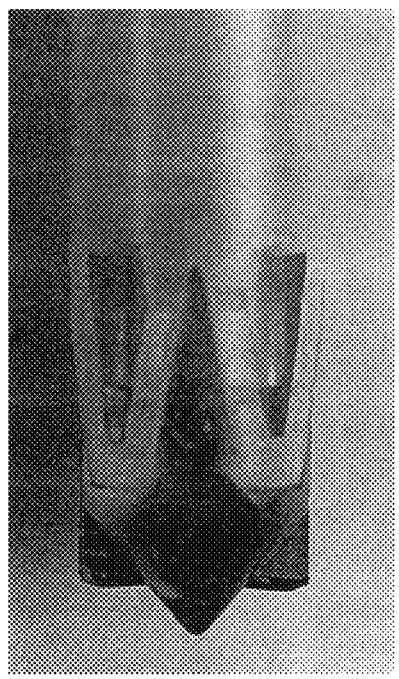
Figure 7C:
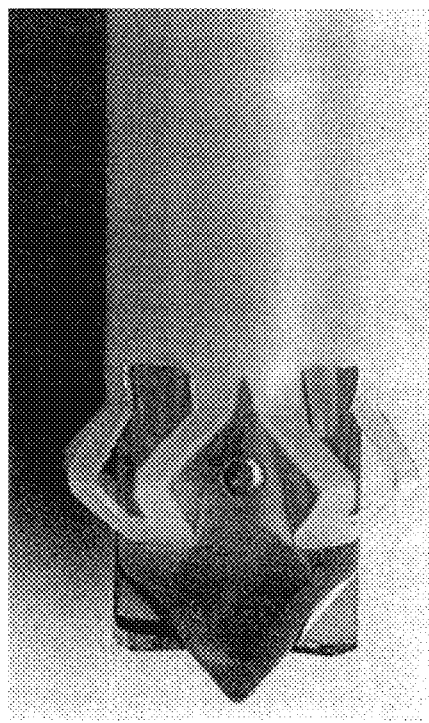

FIG. 9 shows an alternate embodiment of the device shown in FIG. 7a. In this embodiment, trocar 132 is preferably a wider 13 mm trocar (carrying a 13 mm cannula, shown separately in FIG. 10), but with an optional tapered extension 141 that tapers from 13 to 9 mm. This allows a 9 mm paired blade assembly for a relatively smaller incision than with a full 13 mm blade set, but provides a tapered expansion zone to push open the incised tube channel in the body tissue to a full 13 mm opening to receive the wider cannula.

FIGS 11a–b are schematic sectional views of the optional flutter valve aspect of the invention. A silicone plastic, flat sleeve 143, shaped like a duck call reed, when attached 142 to the cannula hub 127, will act as a one way flutter valve to let air and body fluids pass out of the chest cavity, while admitting no air or other matter into the cavity (11a). This valve 143 may optionally be assembled with cannula 128, by attaching a valve base to the hub (such as by ultrasonic or electronic welding), adhesive, or the like), fitting the trocar 132 end into the sleeve end, and then pushing the sleeve into the cannula with the trocar (11b). Upon withdrawal of the trocar, the sleeve is deployed to become the one way exit valve.

FIGS. 12a–c and 13a–b are partial plan details of the overlapped blade points of the blade assemblies of both devices 10 and 100, illustrating the optional common scheme for creating a safe ended zone on the delta point 46 of the extended blades. As described and discussed above, for most of the blade profile of the fully extended blades, there is presented only a single bevel 17° edge, one left, one right (12a, 12b)—very sharp. This serves well for incision generally, but can lead to dangerous over insertion, as discussed. The slight but significant blade overlap at the points (FIG. 12c), without further modification produces a narrow safe zone of relative blade bluntness, in that the cutting edge for this region only is effectively 34°, not just 17°. Optionally, this zone may be widened by grinding each blade point, after grinding the 17° edge, with a second, slightly offset grind, preferably also 17° (though other grind angles may serve as well to produce relatively blunt or even blunter zone). This second grind shows as facet 63 in FIG. 13b and also effectively removes a portion of the delta point shown in dotted line in FIG. 13a. Thus a considerably wider, though overall still small portion of the whole blade profile, safe zone is provided.

Sequence of Operation—Cricar™

Figure 14A:
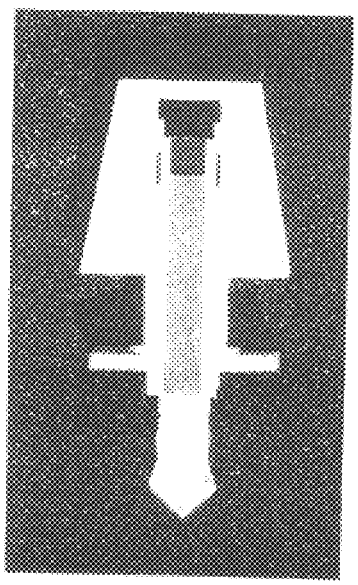
FIGS. 14a–g are photographs of the device shown in FIG. 1, in sequence of operation.

The Cricar™ emergency cricothyrotomy device is used to resolve an acute upper airway obstruction by performing the following sequence of operations:

(FIG. 14a) Remove the bottom of the preferably sealed and sterilized case (not shown—see generally FIGS. 1 & 7 of U.S. Pat. No. 4,291,690) to expose the end of the trocar. The device is preferably dispensed with the twin retractable blades fully extended and ready to insert. Hold the trocar device like a dart with the trigger button up, the thumb on one side of the widest part of the handle and the index and middle finger on the other. Stabilize the larynx (see FIG. 16b) with the opposite hand and push the trocar, slowly and firmly, straight through the skin and cricothyroid membrane. The expanded two piece blade mechanism produces an incision whose width is preferably about one half the circumference of the cannula, thus allowing the tissue to be easily and gently dissected in a single stroke. The sound of air hissing through flutes in the trocar shaft indicates full penetration into the airway. Safety stops contacting the skin prevent over penetration.

Figure 14B:
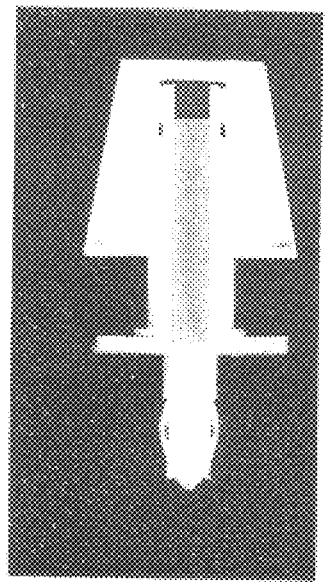

(FIG. 14b) Lift the index finger and compress the trigger button on the side of the handle. This releases a previously spring loaded mechanism which retracts the blades to leave a relatively blunt end on the trocar and also preferably pulls the optional but preferred safety stops back into the handle. Insert the trocar then fully up to the hub of the cannula.

Figure 14C:
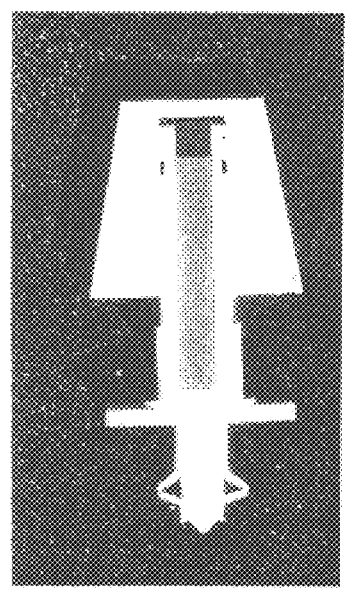
Figure 14D:
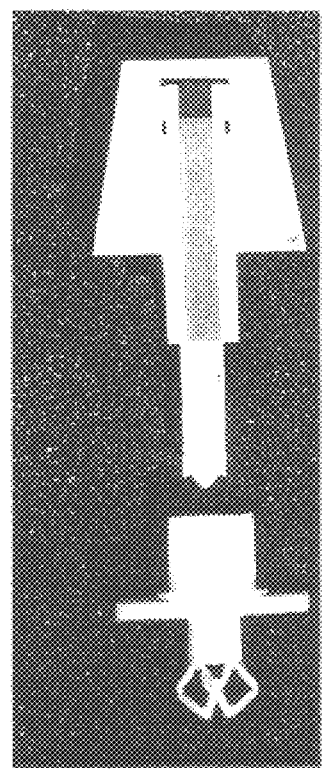

(FIGS. 14c–d) Hold the extracorporeal tabs on the hub of the cannula against the skin with one hand and pull the trocar shaft out of the cannula with the other hand, exercising care not to twist the trocar as it is pulled (as this could prematurely dislodge the collapsible struts from their inletting in such a way as to frustrate the desirable engagement of the distal tips of the struts with the distal end of the inletting during trocar withdrawal). This action causes the network of struts on the end of the cannula to bend and flare outwardly within the trachea to produce firm but gentle retention of the tube within the airway. The light finger spring action of the expanded struts prevents the expulsion of the short, straight cannula as the patient forcefully exhales.

Figure 14E:
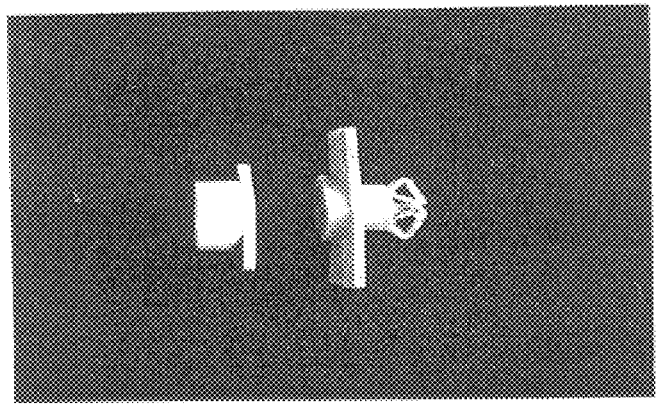
Figure 14F:
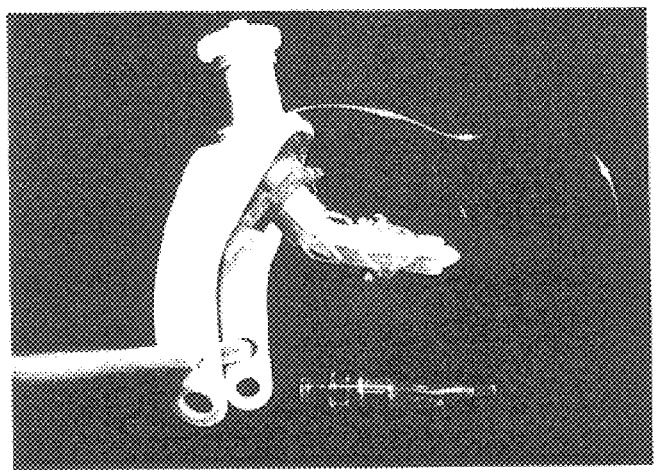
Figure 14G:
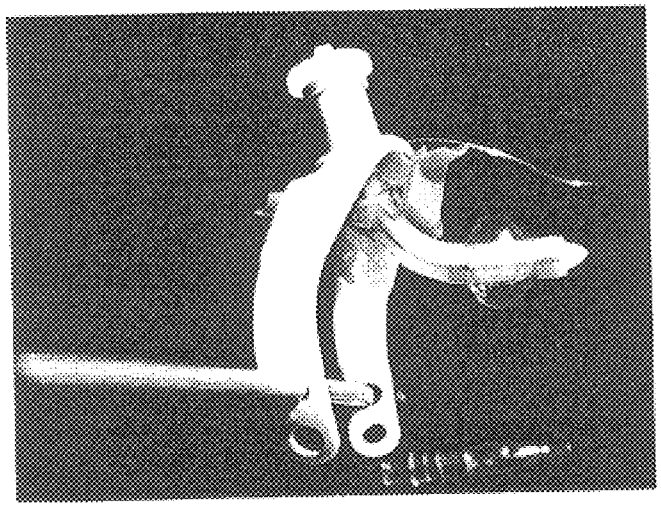

FIG. 14e shows the resuscitator coupling removed from the flare-ended cannula, now securely in place. FIG. 14f shows a standard trach tube now in place in the cannula (note flared struts just above the tube cuff—note also the quadrisegmental cannula has now expanded into a quadrisegmental insertion sleeve, with the removal of the 15 mm resuscitator coupling, to accept the trach tube); FIG. 14g shows the cannula with the network of flared struts and the cannula partially peeled off around the tube still in place.

Sequence of Operation—Thoracar™

The Thoracar™ emergency thoracostomy device is used to resolve a tension pneumothorax or to insert a chest tube by performing the following sequence of operations:

(FIG. 7a) Remove the bottom of the preferably sealed and sterilized case to expose the end of the trocar. The device is preferably dispensed with the twin retractable blades fully extended and ready to insert. Hold the trocar like a screw driver with the trigger button up and the handle pulled tightly against the palm. Locate the superior border of the rib most appropriate for the suspected pneumothorax or hemothorax conditions and stretch the skin up slightly with the thumb of the opposite hand (to later provide a skin flap seal over the incised wound as the tissue rearranges itself post procedure). Place the blade against the skin, parallel with the rib. Push the trocar, slowly and firmly, over the top of the rib, straight into the chest cavity. The two-part expanded blade makes a precise incision that is sized to substantially match the circumference of the self-retaining cannula and thus produces the proper amount of sharp dissection to allow gentle, easy insertion of the trocar. An abrupt drop in tissue resistance as the trocar "pops" into the chest cavity and the sound of air or sight of blood flowing through grooves in the trocar shaft indicate full penetration.

(FIG. 7b) Lift the thumb and compress the button on the side of the handle. This releases the previously spring loaded mechanism which retracts the blades to leave a relatively blunt end on the trocar. Insert the trocar then fully to the hub of the cannula.

Figure 7D:
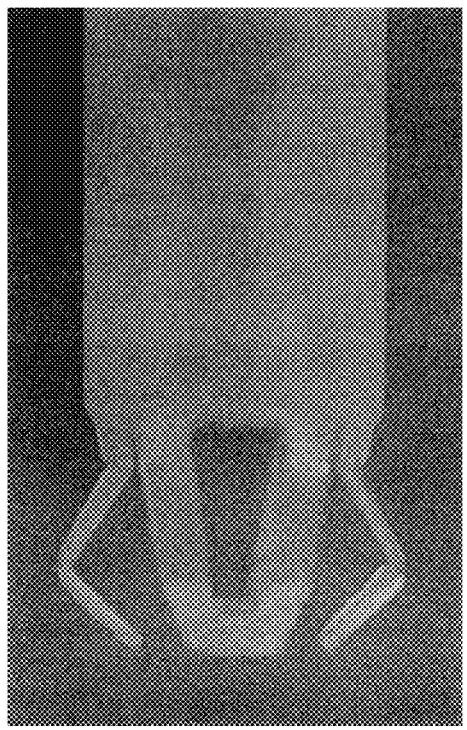
Figure 13A:
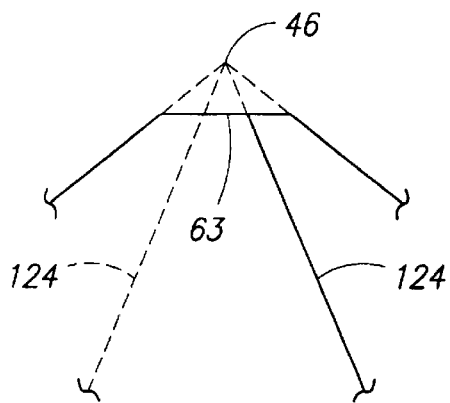
FIGS. 13a–b are partial plan details of the overlapped blade points of the blades shown in FIG. 2.

(FIGS. 7c–d) Hold the hub of the cannula against the skin with one hand and pull the trocar shaft out of the cannula with the other hand, exercising care not to twist the trocar as it is pulled (as this could prematurely dislodge the collapsible struts from their inletting in such a way as to frustrate the desirable engagement of the distal tips of the struts with the distal end of the inletting during trocar withdrawal). This action causes the network of struts on the end of the cannula, which are partially caught in semi-retentive inletting in the trocar tip (note in FIGS. 7a–b), to collapse and bend under the withdrawal force along the molded in living hinge lines and to flare outwardly, producing firm but gentle retention of the tube by its flared end of collapsed and bent network of struts within the chest cavity (FIG. 7d). As the trocar shaft is withdrawn, it deploys an optional removable one way flutter valve on the cannula hub (see FIGS. 11a–b). Insert a standard 36 French chest tube, when necessary. Pull the delivery cannula out and over the extracorporeal excess of the chest tube. Attach chest tube to suction drainage system as appropriate.

Fabrication Notes

The preferred method for making the preferred thin walled, single-use, collapsing polypropylene cannula part is injection molding. Blades are preferably stamped from stainless steel sheet stock, and then sharpened and polished in a precision grinding machine. What is desirable is maximum 'scalpel' sharpness for the given blade material (believed to be about 17.5 degrees of edge angle for stainless steel), so that the double thick, double beveled overlapping blade points will be 'half scalpel sharp'. Sharper than a scalpel is generally not preferred due to increase accidental cutting danger, but would not depart from the scope of the invention; less sharp blades may be made to serve but will present increase penetration resistance with attendant danger of accidental overpenetration as the body wall is penetrated. With that in mind a range of blade edge angles of 17° to 19° are preferred, with 17° more especially preferred.

The handle and shaft portion of the disclosed devices are also preferably injection molded, and have a two piece hermaphrodite part design that allows identical halves to be assembled face to face with the moving parts (retractor shaft, stainless steel cross pins, trigger pin, spring & washer) sandwiched between them. In addition, the blades are also hermaphrodite parts, for mounting face to face. This greatly reduces tooling and production costs of the preferably disposable devices, while increasing uniformity and integrity.

Preferred mating of the variously disclosed half parts is by electronic or ultrasonic welding, or glue, and especially preferred are hermaphrodite molded pin-and-cup structures or the like. These molded structures in the halfparts will, when the preferably identical part halves are turned to face each, be appropriately reciprocally placed, as will be appreciated by those skilled in the art, for mating and secure joinder.

EXAMPLES

Figure 16A:
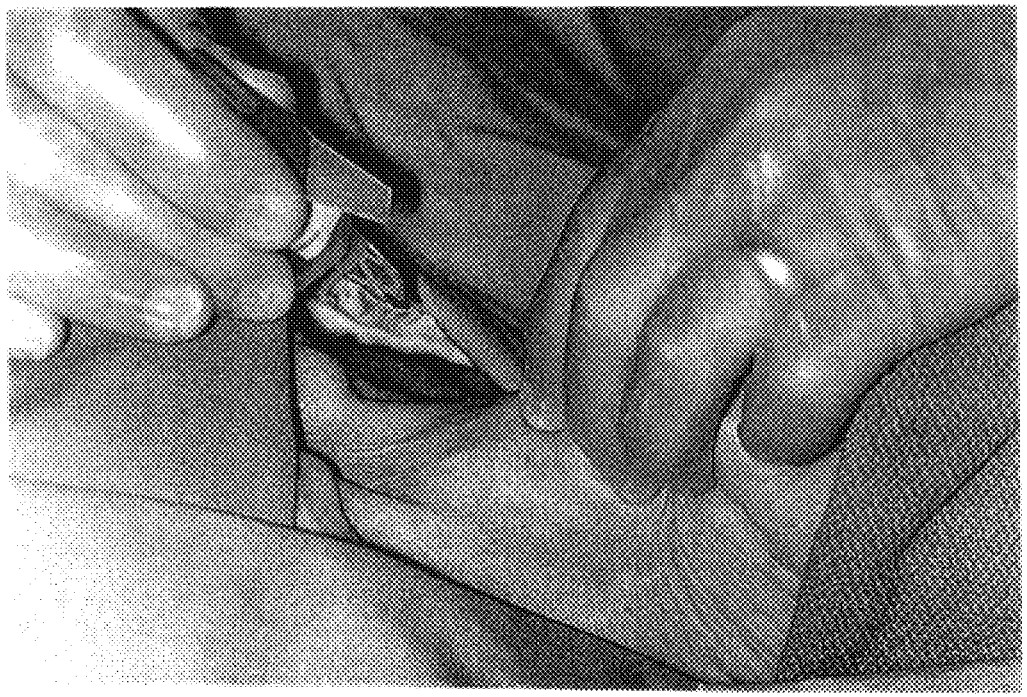
FIGS. 16a–j are photographs of the device shown in FIG. 1, in test sequence of operation.
Figure 16B:
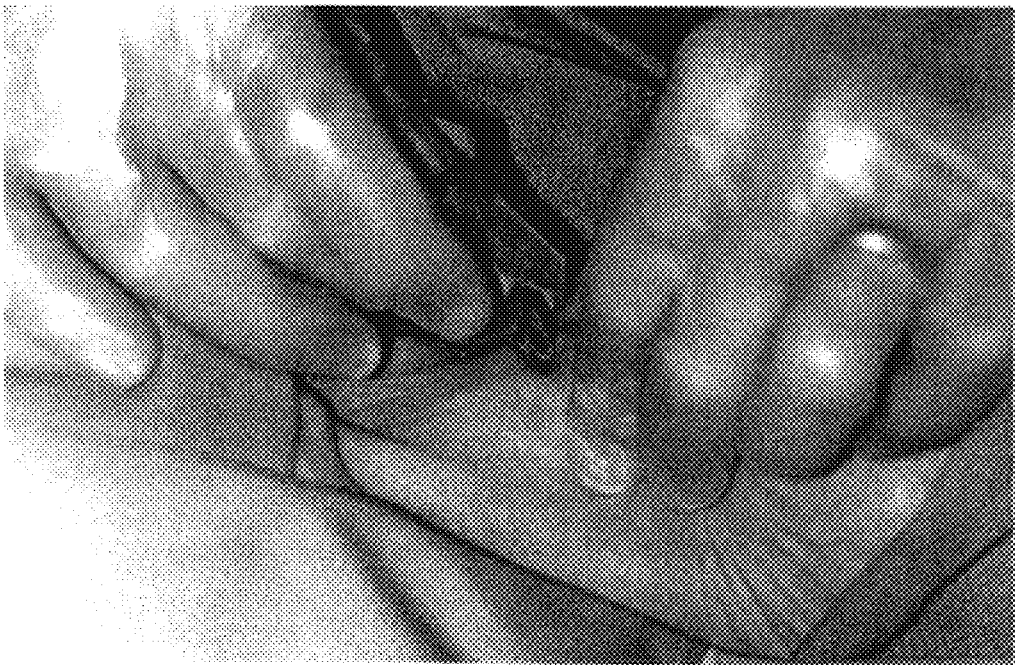
Figure 16C:
Figure 16D:
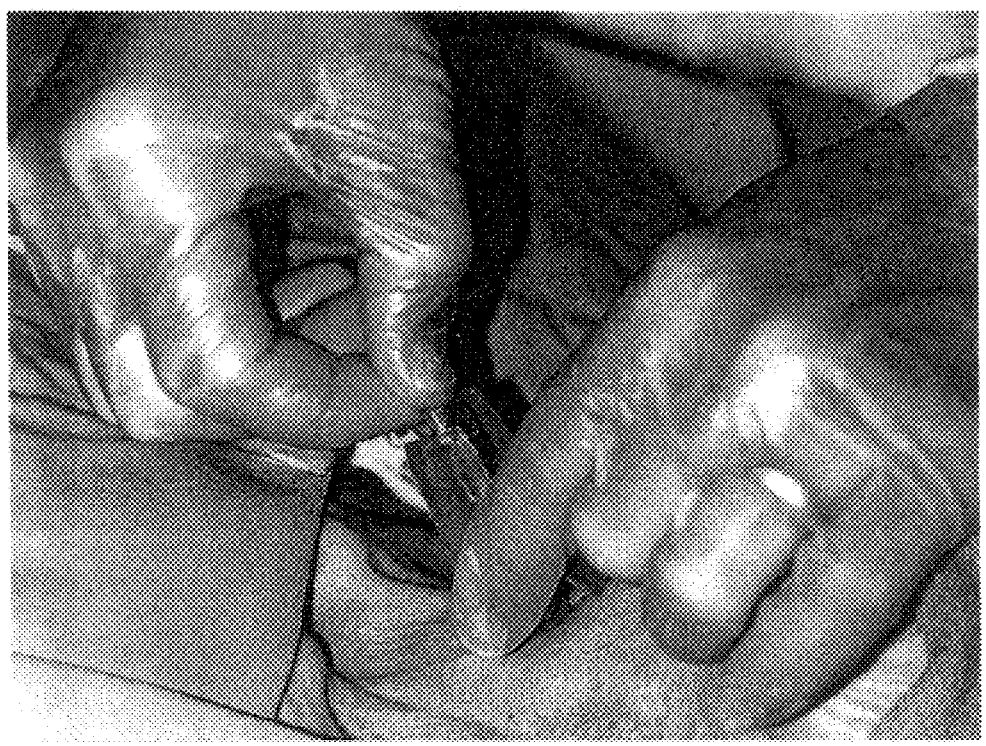
Figure 16E:
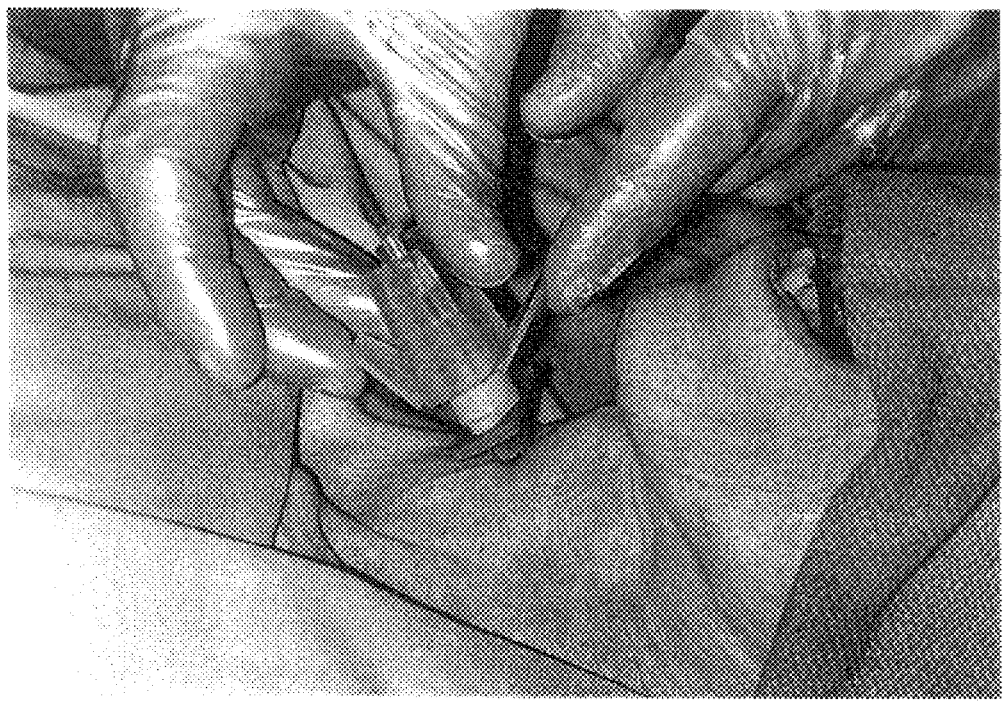
Figure 16F:
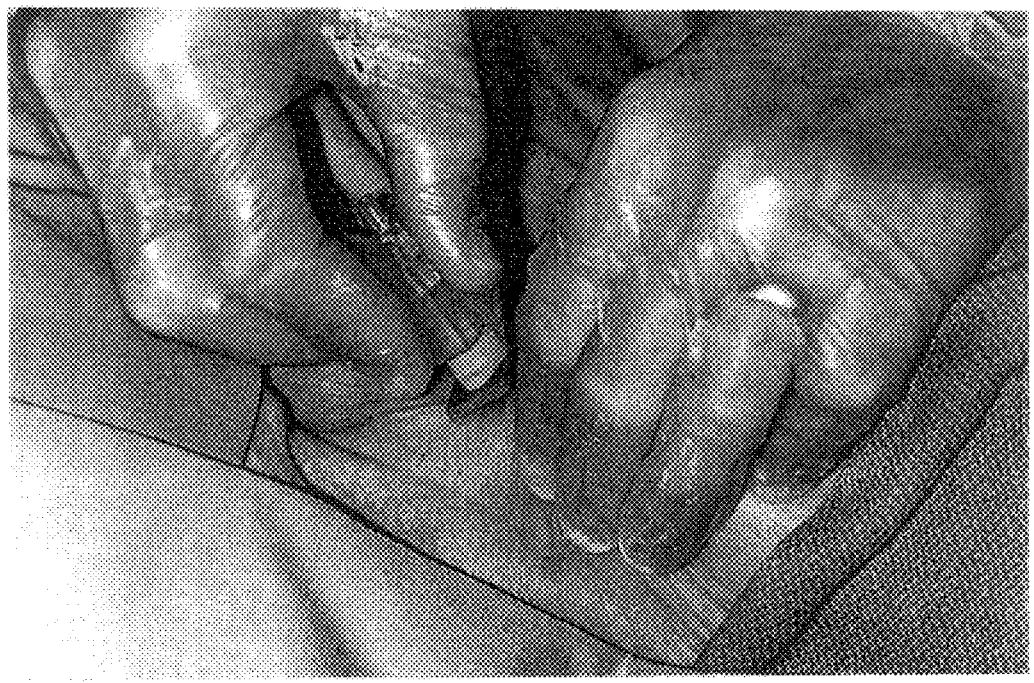
Figure 16G:
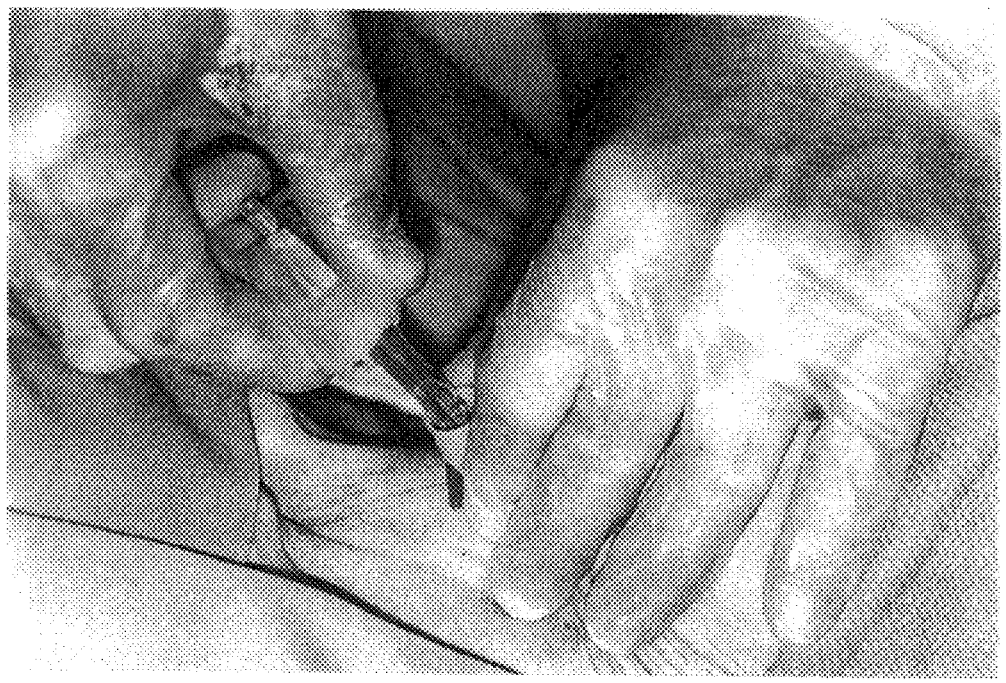
Figure 16H:
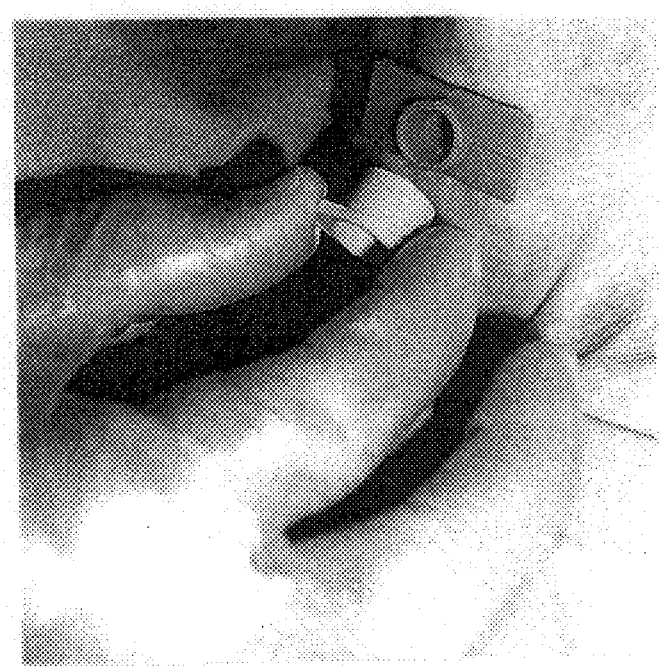
Figure 16I:
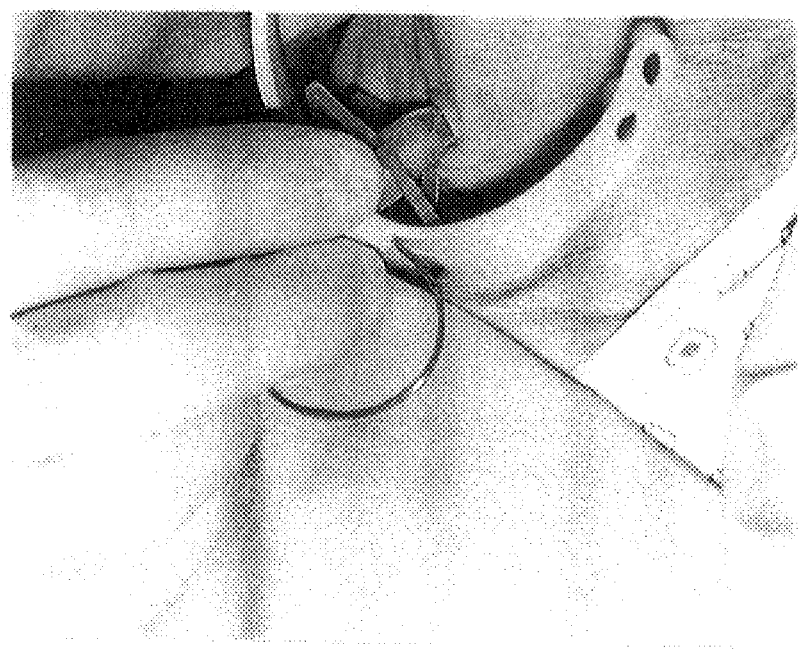
Figure 16J:
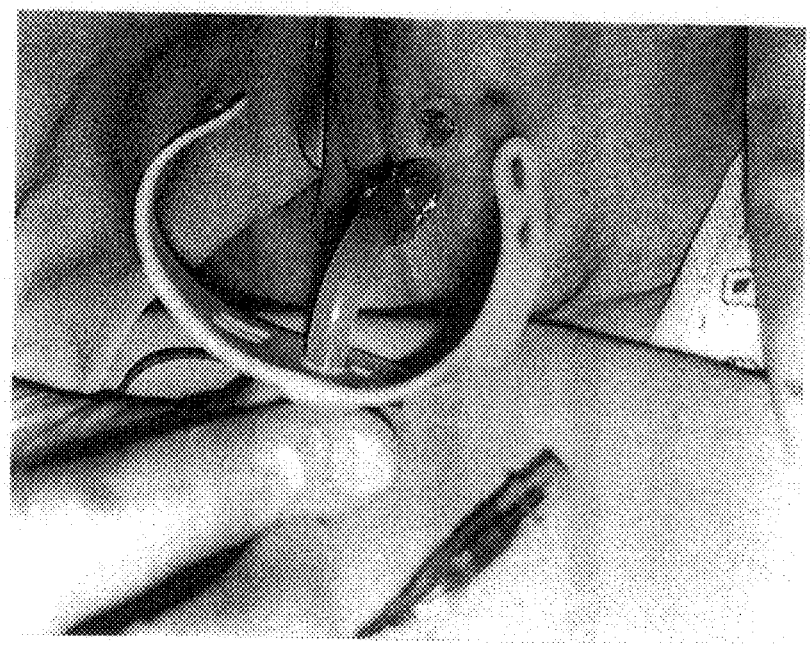

The Cricar device has been tested on human cadavers, as set forth in FIGS. 16a–j, demonstrating the application of an earlier manual (not fitted for spring retraction of blades and tabs) version of the device. In FIG. 16a, the cricothyroid ligament is located by palpation (note expanded and extended cutting blade in device held in hand of operator, with safety tabs extended). In FIGS. 16b–c, the larynx is stabilized as the trocar portion of the device is pushed through the skin and cricothyroid membrane; the safety tabs or stops contact the skin at full safe penetration (blades still extended). In FIG. 16d, the trocar is held in position as the blades are retracted manually by pulling back on the connecting rod (this is now preferably done with a button release of a spring loaded mechanism to retract both the blades and the safety tabs). In FIGS. 16e–f the safety stops are folded back against the handle, and the trocar is then fully inserted. In FIG. 16g, the tabs of the extracorporeal portion of the cannula are firmly held against the skin, and the trocar shaft is withdrawn. FIG. 16h illustrates the optional removal of the optional resuscitator coupling to release the four sections of the cannula, which come fit together to form a double wall, expandable airway tube; with the coupling removed, the cannula is now free to expand as required. In FIG. 16i, a standard cuffed trach tube has been inserted down the cannula; at this point, the cannula may optionally be removed by partial withdrawal of the trach tube and cannula to expose the network of retentive struts on its end; scissors or the trocar blade can cut the network at a central point, and the quadrisegmental cannula can then be unfolded and peeled off (see also FIGS. 14f–g). FIG. 16j shows the relatively small and neat surgical opening produced by the device.

Figure 15A:
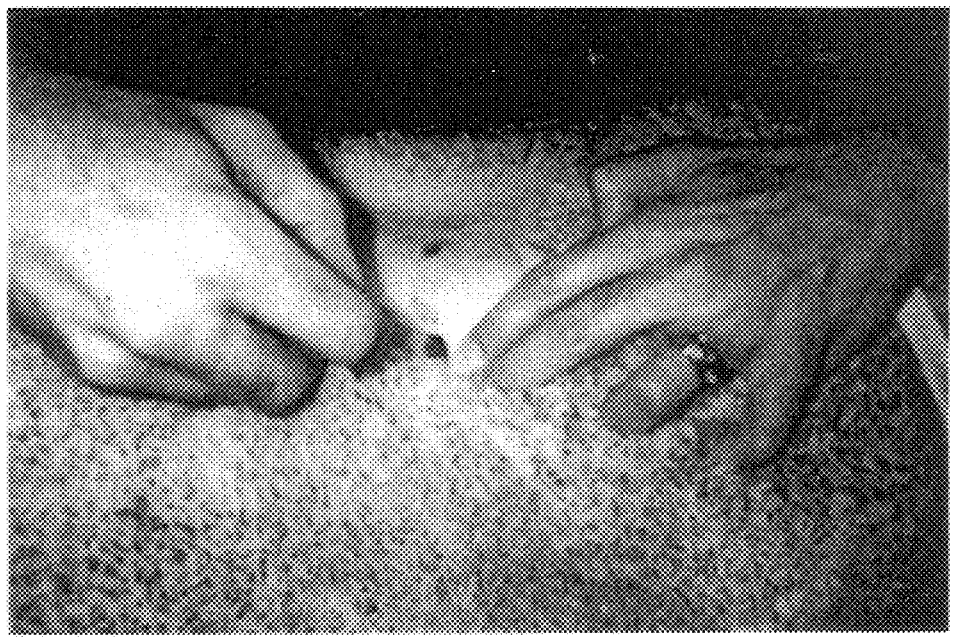
FIGS. 15a–d are photographs of the device shown in FIG. 7, in test sequence of operation.
Figure 15B:
Figure 15C:
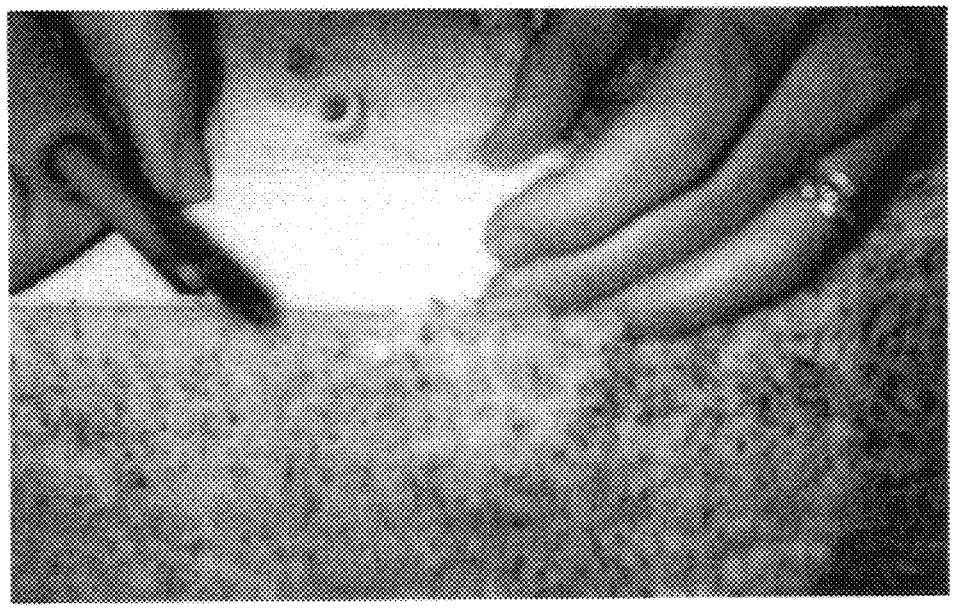
Figure 15D:

A prototype thoracostomy trocar and chest tube delivery system has been tested on a sheep cadaver immediately post mortem, in accordance with acceptable animal testing protocols (see FIGS. 15a–d). Three different operators were able to easily and precisely insert it and deploy its delivery cannula. FIG. 15a shows grip of device shown in FIG. 7 in the hand of an operator, preparatory to insertion; FIG. 15b shows the device inserted almost fully, and the cannula partially inserted (note tight fit of tissue to cannula); FIG. 15c shows the trocar portion of the device now removed, and the cannulafully inserted and selfretained. Upon post procedure dissection (FIG. 15d), no evidence of damage to the lung was noted, even though it was hyper-inflated during the puncture. In addition, no damage to the superior border of the rib was noted. In fact, a concerted effort was made to actually penetrate the hyper-inflated lung directly after the chest was opened, and was not possible despite multiple 10 cm+ straight thrusts of the trocar.

These encouraging results were obtained with a trocar that had a straight 9 mm shaft, two 9 mm blades and delivered a 10 mm O.D. cannula. As it has been recommended that a 36 size French chest tube is the minimum acceptable size for comprehensive management of a severely injured chest where protracted bleeding may occur, the preferred delivery cannula is therefore slightly larger than 13 mm I.D., to accommodate the 13 mm O.D. 36 French tube.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

INDUSTRIAL APPLICABILTY

These low cost disposable cricothyrotomy and thoracostomy trocars and airway tube delivery systems should find use by paramedics, emergency physicians, trauma surgeons, ICU doctors and anesthesiologists, all of whom encounter patients with life threatening stoppage of breath or pneumothoracies regularly. This minimally invasive device can become the standard of care in worldwide use.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

I claim:

1. A surgical cutting tool comprising a cam action retractable blade assembly having two blades, each with a blade edge and an angled blade point, wherein the blades of the blade assembly are two substantially identical blades each having an edge face with a single bevel cutting edge disposed at an angle to a longitudinal axis of the blade, each edge ending in a blade point at a distal end of the blade, the two blades pivotally mounted edge face to edge face upon a pivot pin, the blade points overlapped in an extended blade configuration.

2. The tool of claim 1 wherein the overlapped blade points form a safe zone at a tip of the extended blade configuration.

3. A retractable trocar comprising a cam action retractable blade assembly having two blades, each with a blade edge and an angled blade point, and further comprising a spring and a pushrod engaging the blades to extend the blade assembly against spring tension into a releasably locked position when fully extended.

4. The tool of claim 3 wherein the pushrod is a flexible push-pull linkage.

5. The tool of claim 4 wherein the flexible push-pull linkage is a wire.

6. A retractable trocar comprising a cam action retractable blade assembly having two blades, each with a blade edge and an angled blade point and further comprising a handle enclosing at least a portion of a spring and a pushrod engaging the blades to extend the blade assembly against spring tension into a locked position when fully extended, and a releasable lock mechanism.

* * * * *